United States Patent
Hansen et al.

[11] Patent Number: 5,817,500
[45] Date of Patent: Oct. 6, 1998

[54] ANIMAL FEED ADDITIVES

[75] Inventors: Peter Kamp Hansen; Peter Wagner; Anette Mullertz; Inge Helmer Knap, all of Bagsvaerd, Denmark

[73] Assignee: Novo Nordisk A/S, Bagsvaerd, Denmark

[21] Appl. No.: 886,765

[22] Filed: Jul. 1, 1997

Related U.S. Application Data

[63] Continuation of PCT/DK96/00046, Jan. 26, 1996.

[30] Foreign Application Priority Data

Jan. 26, 1995 [DK] Denmark ................................ 0094/95

[51] Int. Cl.⁶ .............................. C12N 9/24; C12N 15/00; C12N 1/14; C07H 21/04
[52] U.S. Cl. .......................... 435/200; 435/6; 435/252.3; 435/254.11; 435/254.3; 435/320.1; 435/325; 536/23.2; 536/24.3
[58] Field of Search ............................ 435/6, 200, 252.3, 435/254.11, 325, 320.1, 254.3; 536/23.2, 24.3

[56] References Cited

U.S. PATENT DOCUMENTS 5,183,753  2/1993  Wizani et al. ........................... 435/201

FOREIGN PATENT DOCUMENTS

WO 91/04673  4/1991  WIPO .
WO 92/17573  10/1992  WIPO .
WO 93/24621  12/1993  WIPO .
WO 94/21785  9/1994  WIPO .

OTHER PUBLICATIONS

Gomes, et al., Appl. Microbiol Biotechnol, vol. 39, pp. 700–707 (1993).

Lischnig T., et al., Biotechnology Letters, vol. 15, No. 4, pp. 411–414 (Apr. 1993).

Mustafa Alam, et al., Enzyme Microb., vol. 16, pp. 298–302, (Apr. 1994).

Kitpreechavanich V, et al., Dialog Info. Serv., accession No. 4460997 (1984).

Anand L, et al., Dialog Info. Serv., accession No. 7137982 (1989).

Ganju, et al., Canadian Journal of Microbiology, vol. 35, No. 9 pp. 836–842 (1989).

Torronen, et al., Biotechnology, vol. 10, pp. 1461–1465 (Nov. 1992).

Apel, et al., Molecular Plant Microbe Interactions, vol. 6, No. 4, pp. 467–472 (Apr. 1993).

Anand et al., "Purification and Propeties of Xylanase From the Thermophilic Fungus, *Humicola Lanuginosa*", Archives of Biochemistry and Biophysics, vol. 276, No. 2, Feb. 1, pp. 546–553, 1990.

Schlacher et al. (1996) Cloning and Characterization of the Gene for the Thermostable Xylanase XynA from *Thermomyces lanuginosus*. J. Biotechnol. 49:211–218.

*Primary Examiner*—Robert A. Wax
*Assistant Examiner*—Lisa J. Hobbs
*Attorney, Agent, or Firm*—Steve T. Zelson, Esq.; Valeta A. Gregg, Esq.

[57] ABSTRACT

The present invention relates to animal feed additives, which additives comprise a monocomponent xylanase derived from a strain of *Byssochlamus, Chaetomium, Humicola, Malbranchea, Mucor, Myceliophthora, Paecilomyces, Talaromyces, Thermoascus,* or *Thielavia*. In other aspects, the invention relates to monocomponent xylanase preparations, DNA constructs, recombinant expression vectors, host cells, and methods of producing monocomponent xylanase preparations.

7 Claims, 7 Drawing Sheets

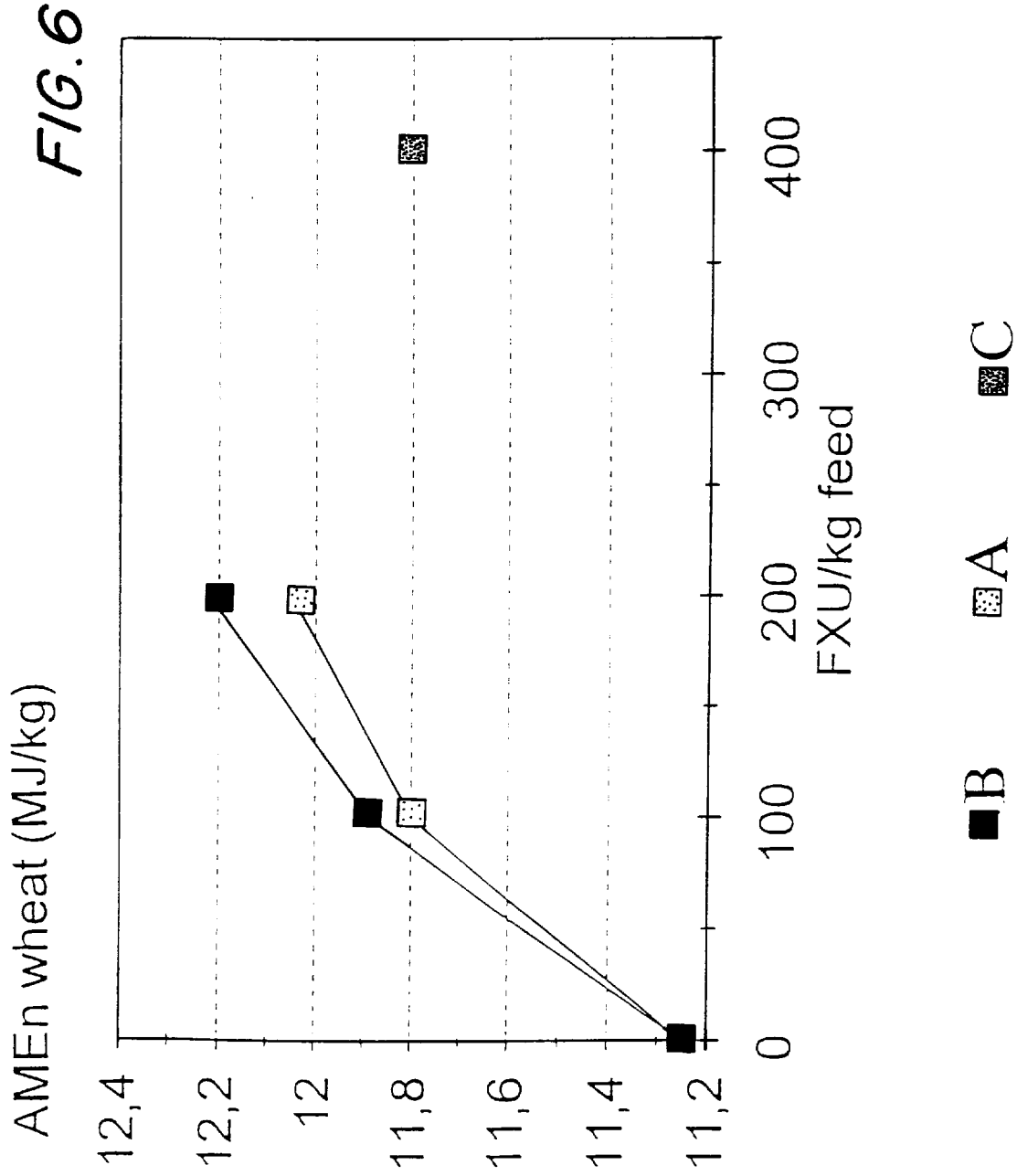

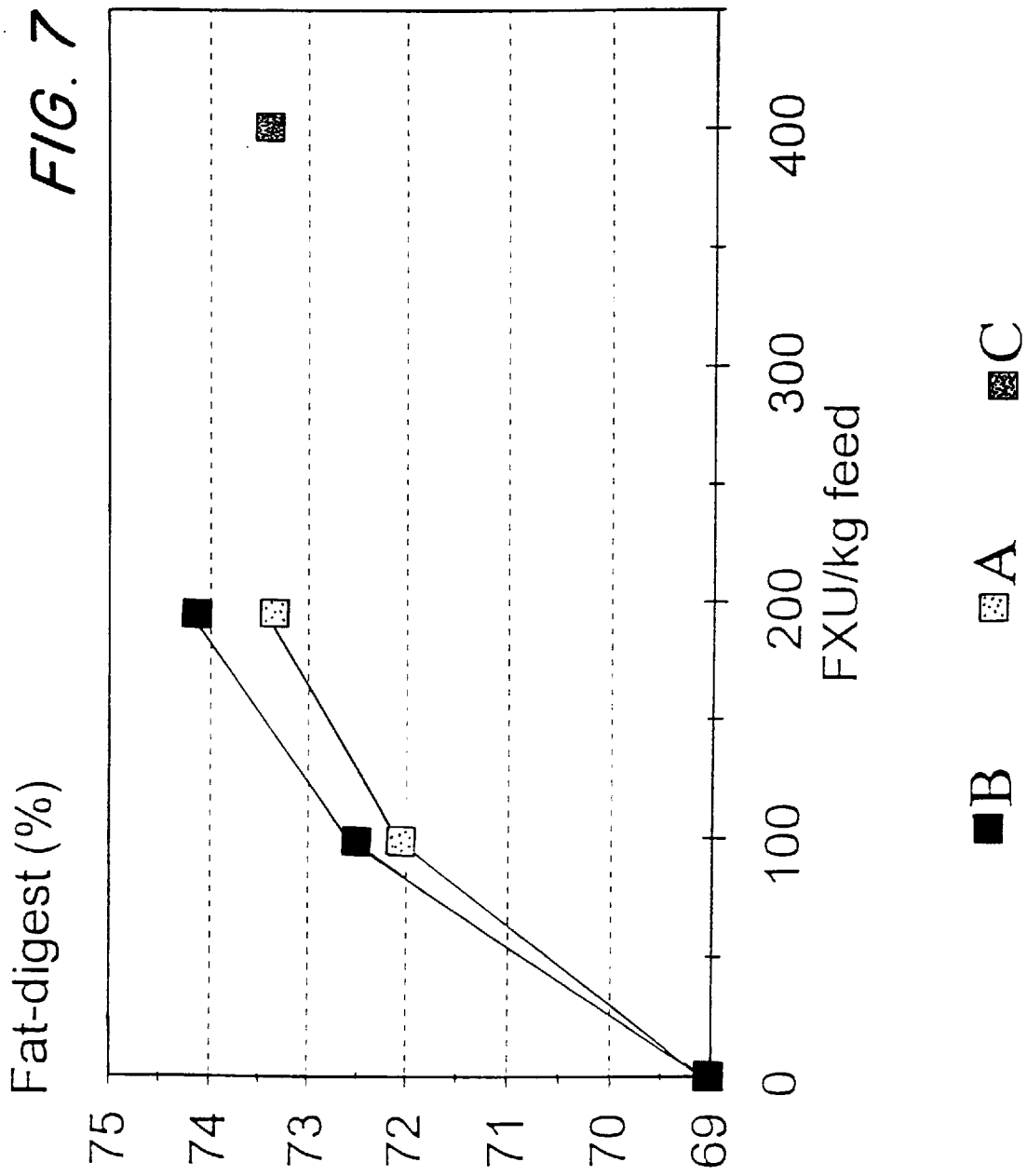

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 983 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Thermomyces lanuginosus
        ( B ) STRAIN: DSM 4109

( i x ) FEATURE:
        ( A ) NAME/KEY: CDS
        ( B ) LOCATION:31..705

( x i ) SEQUENCE DESCRIPTION: SEQ ID NO: 1:

```
TCGGCCCGAC GTCTTGCAAT CCTTGCAGTG ATG GTC GGC TTT ACC CCC GTT GCC        54
                                    Met Val Gly Phe Thr Pro Val Ala
                                     1               5

CTT GCG GCC TTA GCC GCG ACT GGG GCC CTG GCC TTC CCG GCA GGG AAT        102
Leu Ala Ala Leu Ala Ala Thr Gly Ala Leu Ala Phe Pro Ala Gly Asn
     10              15                  20

GCC ACG GAG CTC GAA AAG CGA CAG ACA ACC CCC AAC TCG GAG GGC TGG        150
Ala Thr Glu Leu Glu Lys Arg Gln Thr Thr Pro Asn Ser Glu Gly Trp
 25              30                  35                  40

CAC GAT GGT TAT TAC TAT TCC TGG TGG AGT GAC GGT GGA GCG CAG GCC        198
His Asp Gly Tyr Tyr Tyr Ser Trp Trp Ser Asp Gly Gly Ala Gln Ala
             45                  50                  55

ACG TAC ACC AAC CTG GAA GGC GGC ACC TAC GAG ATC AGC TGG GGA GAT        246
Thr Tyr Thr Asn Leu Glu Gly Gly Thr Tyr Glu Ile Ser Trp Gly Asp
             60                  65                  70

GGC GGT AAC CTC GTC GGT GGA AAG GGC TGG AAC CCC GGC CTG AAC GCA        294
Gly Gly Asn Leu Val Gly Gly Lys Gly Trp Asn Pro Gly Leu Asn Ala
             75                  80                  85

AGA GCC ATC CAC TTT GAG GGT GTT TAC CAG CCA AAC GGC AAC AGC TAC        342
Arg Ala Ile His Phe Glu Gly Val Tyr Gln Pro Asn Gly Asn Ser Tyr
     90              95                 100

CTT GCG GTC TAC GGT TGG ACC CGC AAC CCG CTG GTC GAG TAT TAC ATC        390
Leu Ala Val Tyr Gly Trp Thr Arg Asn Pro Leu Val Glu Tyr Tyr Ile
105             110                 115                 120

GTC GAG AAC TTT GGC ACC TAT GAT CCT TCC TCC GGT GCT ACC GAT CTA        438
Val Glu Asn Phe Gly Thr Tyr Asp Pro Ser Ser Gly Ala Thr Asp Leu
                125                 130                 135

GGA ACT GTC GAG TGC GAC GGT AGC ATC TAT CGA CTC GGC AAG ACC ACT        486
Gly Thr Val Glu Cys Asp Gly Ser Ile Tyr Arg Leu Gly Lys Thr Thr
                140                 145                 150

CGC GTC AAC GCA CCT AGC ATC GAC GGC ACC CAA ACC TTC GAC CAA TAC        534
Arg Val Asn Ala Pro Ser Ile Asp Gly Thr Gln Thr Phe Asp Gln Tyr
            155                 160                 165

TGG TCG GTC CGC CAG GAC AAG CGC ACC AGC GGT ACC GTC CAG ACG GGC        582
Trp Ser Val Arg Gln Asp Lys Arg Thr Ser Gly Thr Val Gln Thr Gly
        170                 175                 180

TGC CAC TTC GAC GCC TGG GCT CGC GCT GGT TTG AAT GTC AAC GGT GAC        630
Cys His Phe Asp Ala Trp Ala Arg Ala Gly Leu Asn Val Asn Gly Asp
185                 190                 195                 200

CAC TAC TAC CAG ATC GTT GCA ACG GAG GGC TAC TTC AGC AGC GGC TAT        678
His Tyr Tyr Gln Ile Val Ala Thr Glu Gly Tyr Phe Ser Ser Gly Tyr
                205                 210                 215
```

```
GCT  CGC  ATC  ACC  GTT  GCT  GAC  GTG  GGC  TAAGACGTAA  CCTGGTGGTG                    725
Ala  Arg  Ile  Thr  Val  Ala  Asp  Val  Gly
               220                      225

ATCTCGCGAG  GCAACAGCCA  AGAATGTCGT  CAGATGTGCC  GGTTGAAGGT  ATTCAATCAG                  785

CATATCTGTC  TGCCCTTGCG  AGTGATACTT  TGGAGGACTG  TGGAGAACTT  TGTGCGAGCC                  845

TGGCCAGGAT  CAGTAGTTGC  TTTGCGGTGT  TTTGCTCCCT  ATTCTCGTGA  AAAAATTGTT                  905

ATTGCTTCGT  TGTCTAGTGT  ACATAGCCGA  GCAATTGAGG  CCTCACGCTT  GGGAAAAAAA                  965

AAAAAAAAAA  AAAAAAA                                                                    983
```

( 2 ) INFORMATION FOR SEQ ID NO: 2:

( i ) SEQUENCE CHARACTERISTICS:
        ( A ) LENGTH: 225 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Val  Gly  Phe  Thr  Pro  Val  Ala  Leu  Ala  Ala  Leu  Ala  Ala  Thr  Gly
 1              5                        10                       15

Ala  Leu  Ala  Phe  Pro  Ala  Gly  Asn  Ala  Thr  Glu  Leu  Glu  Lys  Arg  Gln
              20                        25                       30

Thr  Thr  Pro  Asn  Ser  Glu  Gly  Trp  His  Asp  Gly  Tyr  Tyr  Tyr  Ser  Trp
              35                        40                       45

Trp  Ser  Asp  Gly  Gly  Ala  Gln  Ala  Thr  Tyr  Thr  Asn  Leu  Glu  Gly  Gly
         50                        55                       60

Thr  Tyr  Glu  Ile  Ser  Trp  Gly  Asp  Gly  Gly  Asn  Leu  Val  Gly  Gly  Lys
65                        70                       75                       80

Gly  Trp  Asn  Pro  Gly  Leu  Asn  Ala  Arg  Ala  Ile  His  Phe  Glu  Gly  Val
              85                        90                       95

Tyr  Gln  Pro  Asn  Gly  Asn  Ser  Tyr  Leu  Ala  Val  Tyr  Gly  Trp  Thr  Arg
              100                       105                      110

Asn  Pro  Leu  Val  Glu  Tyr  Tyr  Ile  Val  Glu  Asn  Phe  Gly  Thr  Tyr  Asp
              115                       120                      125

Pro  Ser  Ser  Gly  Ala  Thr  Asp  Leu  Gly  Thr  Val  Glu  Cys  Asp  Gly  Ser
         130                       135                      140

Ile  Tyr  Arg  Leu  Gly  Lys  Thr  Thr  Arg  Val  Asn  Ala  Pro  Ser  Ile  Asp
145                       150                      155                      160

Gly  Thr  Gln  Thr  Phe  Asp  Gln  Tyr  Trp  Ser  Val  Arg  Gln  Asp  Lys  Arg
              165                       170                      175

Thr  Ser  Gly  Thr  Val  Gln  Thr  Gly  Cys  His  Phe  Asp  Ala  Trp  Ala  Arg
              180                       185                      190

Ala  Gly  Leu  Asn  Val  Asn  Gly  Asp  His  Tyr  Tyr  Gln  Ile  Val  Ala  Thr
         195                       200                      205

Glu  Gly  Tyr  Phe  Ser  Ser  Gly  Tyr  Ala  Arg  Ile  Thr  Val  Ala  Asp  Val
         210                       215                      220

Gly
225
```

1

ANIMAL FEED ADDITIVES

CROSS-REFERENCE TO RELATED APPLICATIONS

This application is a continuation of Ser. No. PCT/DK96/00046 filed Jan. 26, 1996 and claims priority under 35 U.S.C. 119 of Danish application serial no. 0094/95 filed Jan. 26, 1995, the contents of which are fully incorporated herein by reference.

TECHNICAL FIELD

The present invention relates to animal feed additives, which additives comprise a monocomponent xylanase derived from a strain of *Byssochlamus, Chaetomium, Humicola, Malbranchea, Mucor, Myceliophthora, Paecilomyces, Talaromyces, Thermoascus,* or *Thielavia*. In other aspects, the invention relates to monocomponent xylanase preparations, DNA constructs, recombinant expression vectors, host cells, and methods of producing monocomponent xylanase preparations.

BACKGROUND ART

The types and amount of plant raw materials which can be used as components in animal feeds will often be limited by the ability of the animals to digest them. Feed enhancing enzymes are enzymes, usually of microbial origin, that by improving feed digestibility are able to increase the efficiency of its utilization.

Xylanolytic enzymes (EC 3.2.1.8) are well known as feed enhancing enzymes. Xylanases obtained from strains of *Bacillus, Aspergillus, Trichoderma, Acremonium* have been reported. Moreover, an enzyme preparation obtained by submerged fermentation of *Humicola insolens* have been marketed (Bio-Feed™ Plus, available from Novo Nordisk A/S, Denmark).

Xylanase preparations obtained from strains of the fungus *Thermomyces lanuginosus* (Syn. *Humicola lanuginosa*) have been described [cf. Lischnig T, Purkarthofer H and Steiner W; *Biotechnology Letters* 1993 15 (4) 411–414; Gomes J, Purkarthofer H, Hayn M, Kapplmüuller J, Sinner M, and Steiner W, *Appl. Microbiol. Biotechnol.* 1993 39 700–707]. However, the use of a *Thermomyces lanuginosus* xylanase as a feed enhancing enzyme has never been disclosed.

Moreover, the xylanase preparations described in the prior art all relates to complex enzyme preparations comprising multiple enzyme components. Monocomponent xylanase preparations derived from *Thermomyces* by use of recombinant DNA technology have never been disclosed.

For many applications, the use of complex enzyme preparations is considered beneficial due to a synergistic effect arising from the co-operative action of multiple components. For some applications, e.g. the conversion of lignocellulose into liquid feedstocks or fuel, the processing of foods, and in particular for increasing digestibility of animal feed, a mixture of xylanolytic and cellulytic enzymes is regarded having optimal performance [Alam M, Gomes I, Mohiuddin G, & Hoq MM; *Enzyme Microb. Technol.* 1994 16 298–302].

SUMMARY OF THE INVENTION

According to the present invention it has now been found that when compared to conventional feed enhancing enzymes, the xylanase derived from *Thermomyces lanuginosus* is an excellent feed enhancing enzyme which shows significant improvement of the feed utilization when added to animal feed. Moreover, owing to an excellent thermostability, the xylanase preparation derived from *Thermomyces lanuginosus* is particularly well suited for being processed into feed additives at conditions preventing microbial infections, in particular *Salmonella* infection. It has also been found that the xylanase derived from *Thermomyces lanuginosus* exerts a significant reduction of digesta viscosity, which indicates a significant improvement in the chicken feed conversion efficiency.

Finally it has surprisingly been found that the recombinantly produced *Thermomyces* xylanase is significantly more thermostable than the native xylanase, which makes the recombinantly produced xylanase particularly well suited for being processed into feed additives at conditions preventing microbial infections, in particular *Salmonella* infection.

Therefore it is an object of the present invention to provide a monocomponent xylanase preparation, which xylanase component is obtained by recombinant DNA techniques from a strain of *Thermomyces* or a related genus.

Accordingly, in its first aspect, the present invention provides an animal feed additive, which additive comprises a monocomponent xylanase derived from a strain of *Byssochlamus, Chaetomium, Humicola, Malbranchea, Mucor, Myceliophthora, Paecilomyces, Talaromyces, Thermoascus,* or *Thielavia*.

In another aspect, the present invention provides a monocomponent xylanase preparation, in which preparation the xylanase component is derived from a strain of *Byssochlamus, Chaetomium, Humicola, Malbranchea, Mucor, Myceliophthora, Paecilomyces, Talaromyces, Thermoascus,* or *Thielavia*.

In a further aspect, the invention relates to a DNA construct comprising a DNA sequence encoding a xylanase component, which DNA sequence comprises:

a) the xylanase encoding part of the DNA sequence presented as SEQ ID NO: 1, or the DNA sequence obtainable from the plasmid in the strain *Saccharomyces cerevisiae* DSM 10133; or b) a DNA sequence analogue to the xylanase encoding part of the DNA sequence presented as SEQ ID NO: 1, or to the DNA sequence obtainable from the plasmid in the strain *Saccharomyces cerevisiae* DSM 10133, which analog DNA sequence either
  i) is homologous to the xylanase encoding part of the DNA sequence presented as SEQ ID NO: 1, or to the DNA sequence obtainable from the plasmid in the strain *Saccharomyces cerevisiae* DSM 10133; or
  ii) hybridizes with the same oligonucleotide probe as the xylanase encoding part of the DNA sequence presented as SEQ ID NO: 1, or with the DNA sequence obtainable from the plasmid in the strain *Saccharomyces cerevisiae* DSM 10133; or
  iii) encodes a polypeptide which is at least 70% homologous to the polypeptide encoded by the DNA sequence presented as SEQ ID NO: 1, or to the DNA sequence obtainable from the plasmid in the strain *Saccharomyces cerevisiae* DSM 10133; or
  iv) encodes a polypeptide which is immunologically reactive with an antibody raised against the purified xylanase derived from the strain *Thermomyces lanuginosus*, DSM 4109, or encoded by the DNA sequence presented as SEQ ID NO: 1, or the DNA sequence obtainable from the plasmid in the strain *Saccharomyces cerevisiae* DSM 10133.

In yet further aspects, the invention relates to an expression vector harbouring a DNA construct of the invention, a host cell comprising the DNA construct or expression vector, and a method of producing a mono component xylanase preparation of the invention, which method comprises culturing said host cell under conditions permitting the production of the enzyme, and recovering the enzyme from the culture.

BRIEF DESCRIPTION OF DRAWINGS

The present invention is further illustrated by reference to the accompanying drawings, in which:

FIG. 6 shows the AMEn value of wheat (MJ/kg) as a function of xylanase addition (FXU/kg feed); (A) *Thermomyces lanuginosus* monocomponent xylanase preparation; (B) native *Thermomyces lanuginosus* xylanase preparation; (C) reference (Bio-Feed Plus CT, a product of Novo Nordisk A/S, Denmark; a multicomponent enzyme preparation obtained by cultivation of Humicola insolens); and FIG. 7 shows the fat digestion (%) in the experimental diet, as a function of xylanase addition (FXU/kg feed); (A) *Thermomyces lanuginosus* monocomponent xylanase preparation; (B) native *Thermomyces lanuginosus* xylanase preparation; (C) reference (Bio-Feed Plus CT, a product of Novo Nordisk A/S, Denmark; a multicomponent enzyme preparation obtained by cultivation of *Humicola insolens*).

DETAILED DISCLOSURE OF THE INVENTION

Animal Feed Additives

Figure 1:
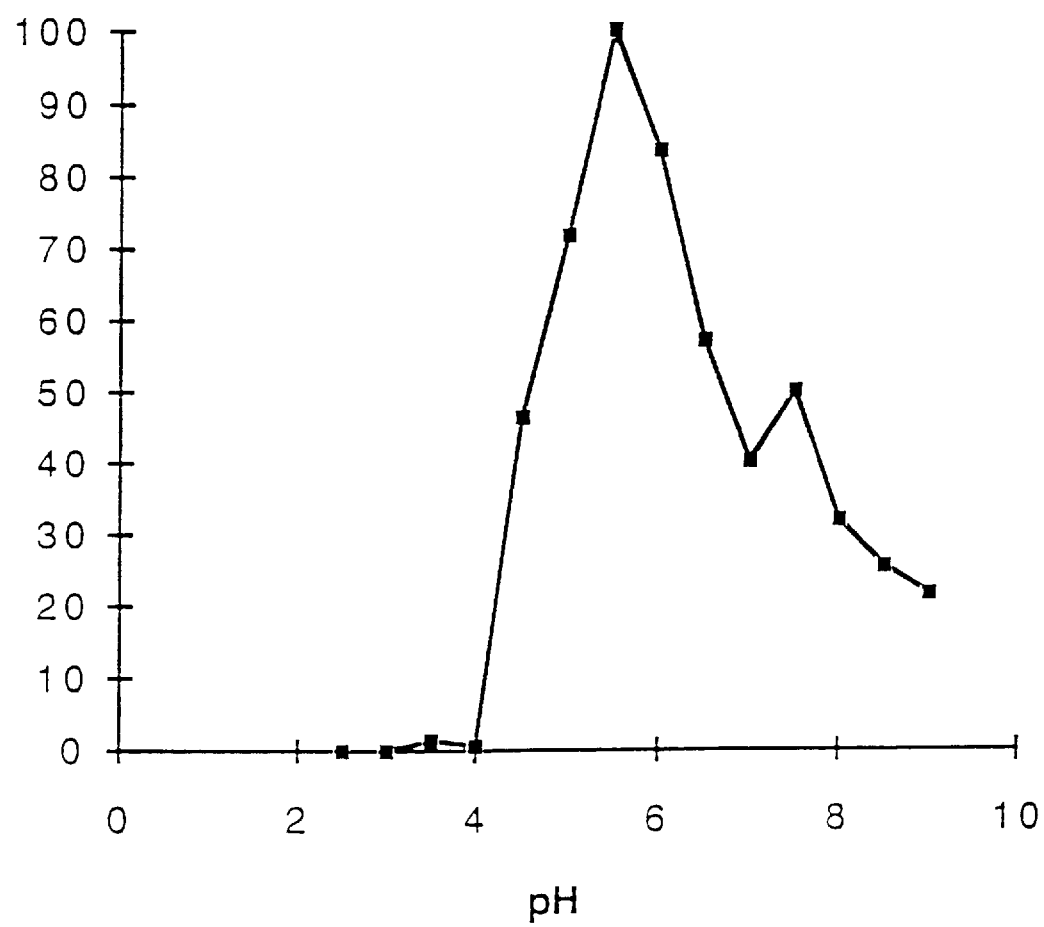
FIG. 1 shows the relative xylanolytic activity (%) of a monocomponent xylanase of the invention, determined at 30° C. in the range of from pH 2.5 to 9. It appears that the enzyme has a pH optimum in the range 4.5–7.5, more specifically the range 5.0–6.5, around pH6.

When added to animal feed, feed enhancing enzymes improve the in vivo break-down of plant cell wall material partly due to a reduction of the intestinal viscosity (Bedford et al., *Proceedings of the* 1st *Symposium on Enzymes in Animal Nutrition*, 1993, pp. 73–77), whereby a better utilization of the plant nutrients by the animal is achieved. Thereby, the growth rate and/or feed conversion ratio (i.e. the weight of ingested feed relative to weight gain) of the animal is improved.

In the context of this invention, an animal feed additive is an enzyme preparation comprising one or more feed enhancing enzyme(s) and suitable carriers and/or excipients, and which enzyme preparation is provided in a form that is suitable for being added to animal feed. The animal feed additive of the invention may be prepared in accordance with methods known in the art and may be in the form of a dry or a liquid preparation. The enzyme to be included in the preparation, may optionally be stabilized in accordance with methods known in the art.

In the context of this invention, an animal feed additive comprising a monocomponent xylanase is an enzyme preparation provided in a form suitable for being added to animal feed, in which preparation essentially all of the xylanolytic activity (i.e. the xylanolytic activity detectable) is owing to a single xylanase component.

The animal feed additive of the invention may be a granulated enzyme product which may readily be mixed with feed components, or more preferably, form a component of a pre-mix. The granulated enzyme product may be coated or uncoated. The particle size of the enzyme granulates preferably is compatible with that of feed and pre-mix components. This provides a safe and convenient mean of incorporating enzymes into feeds.

Also, the animal feed additive of the invention may be a stabilized liquid composition, which may be an aqueous or oil-based slurry.

The animal feed additive of the invention may exert its effect either in vitro (by modifying components of the feed) or in vivo. The feed additive of the invention is particularly suited for addition to animal feed compositions containing high amounts of arabinoxylans and glucuronoxylans, e.g. feed containing cereals such as barley, wheat, rye or oats or maize.

Monocomponent Xylanase Preparations

The present invention provides an animal feed additive, which additive comprises a monocomponent xylanase derived from a strain of *Byssochlamus, Chaetomium, Humicola, Malbranchea, Mucor, Myceliophthora, Paecilomyces, Talaromyces, Thermoascus,* or *Thielavia.*

In a preferred embodiment, the animal feed additive of the invention comprises a monocomponent xylanase derived from a strain of *Thermomyces*, in particular from a strain of *Thermomyces lanuginosus*, most preferred from the strain *Thermomyces lanuginosus*, DSM 4109, or a mutant or a variant thereof.

In a more specific embodiment, the xylanase has immunochemical properties identical or partially identical (i.e. at least partially identical) to those of a purified xylanase, which is either a) derived from the strain *Thermomyces lanuginosus*, DSM 4109; or b) encoded by the xylanase encoding part of the DNA sequence presented as SEQ ID NO: 1; or c) encoded by the DNA sequence obtainable from the plasmid in the strain *Saccharomyces cerevisiae* DSM 10133.

Preferably the monocomponent xylanase is derived from a host cell carrying a gene encoding the xylanase component. In particular the monocomponent xylanase may be a) encoded by the DNA sequence presented as SEQ ID NO: 1, or by the DNA sequence obtainable from the plasmid in the strain *Saccharomyces cerevisiae* DSM 10133; or b) encoded by a DNA sequence analogue to the xylanase encoding part of the DNA sequence presented as SEQ ID NO: 1, or to the DNA sequence obtainable from the plasmid in the strain *Saccharomyces cerevisiae* DSM 10133, which analog DNA sequence either i) is homologous to the xylanase encoding part of the DNA sequence presented as SEQ ID NO: 1, or to the DNA sequence obtainable from the plasmid in the strain *Saccharomyces cerevisiae* DSM 10133; or ii) hybridizes with the same oligonucleotide probe as the xylanase encoding part of the DNA sequence presented as SEQ ID NO: 1, or with the DNA sequence obtainable from the plasmid in the strain *Saccharomyces cerevisiae* DSM 10133; or iii) encodes a polypeptide which is at least 70% homologous to the polypeptide encoded by the DNA sequence presented as SEQ ID NO: 1, or to the DNA sequence obtainable from the plasmid in the strain *Saccharomyces cerevisiae* DSM 10133; or iv) encodes a polypeptide which is immunologically reactive with an antibody raised against the purified xylanase derived from the strain *Thermomyces lanuginosus*, DSM 4109, or encoded by the DNA sequence presented as SEQ ID NO: 1, or the DNA sequence obtainable from the plasmid in the strain *Saccharomyces cerevisiae* DSM 10133.

In yet more preferred embodiments the monocomponent xylanase may further be characterized by a) having a residual enzyme activity of more than 96% after incubation for 60 minutes at pH 6.0 and 60° C.;

b) having a residual enzyme activity of more than 83% after incubation for 60 minutes at pH 6.0 and 65° C.;

c) having a residual enzyme activity of more than 20% after incubation for 60 minutes at pH 6.0 and 70° C.; and/or d) having a residual enzyme activity of more than 10% after incubation for 60 minutes at pH 6.0 and 75° C.

Analogous DNA Sequences

As defined herein, a DNA sequence analogue to the xylanase encoding part of the DNA sequence presented as SEQ ID NO: 1 is intended to indicate any DNA sequence encoding a xylanolytic enzyme, which enzyme has one or more of the properties cited under (i)–(iv), above.

The analogous DNA sequence may preferably be isolated from another or related (e.g. the same) organism producing the xylanase component, on the basis of the xylanase encoding part of the DNA sequence shown in SEQ ID NO: 1, or a suitable subsequence (such as 20–500 bp) thereof, e.g. using the procedures described herein, and thus, e.g. be an allelic or species variant of the DNA sequence comprising the DNA sequence presented herein.

Alternatively, the analogous sequence may be constructed on the basis of the xylanase encoding part of the DNA sequence presented as SEQ ID NO: 1, or any subsequence thereof, e.g. by introduction of nucleotide substitutions which do not give rise to another amino acid sequence of the xylanolytic enzyme encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., *Protein Expression and Purification,* 2 1991 95–107.

It will be apparent to persons skilled in the art that such substitutions can be made outside the regions critical to the function of the molecule and still result in an active xylanolytic enzyme. Amino acids essential to the activity of the xylanase encoded by the DNA construct of the invention, and therefore preferably not subject to substitution, may be identified according to procedures known in the art, such as site-directed mutagenesis or alanine-scanning mutagenesis (cf. e.g. Cunningham and Wells, *Science* 1989 244 1081–1085). In the latter technique mutations are introduced at every residue in the molecule, and the resultant mutant molecules are tested for biological (i.e. proteolytic) activity to identify amino acid residues that are critical to the activity of the molecule. Sites of substrate-enzyme interaction can also be determined by analysis of crystal structure as determined by such techniques as nuclear magnetic resonance analysis, crystallography or photo affinity labelling (cf. e.g. de Vos et al., *Science* 1992 255 306–312; Smith et al., *J. Mol. Biol.* 1992 224 899–904; Wlodaver et al., *FEBS Lett.* 1992 309 59–64).

It will be understood that the xylanase encoding part of the DNA sequence presented as SEQ ID NO: 1, or any subsequence thereof, may be used as probes for isolating the entire DNA sequence encoding the xylanolytic enzyme, e.g. the DNA sequence presented as SEQ ID NO: 1.

The homology referred to in i) above is determined as the degree of identity between the two sequences indicating a derivation of the first sequence from the second. The homology may suitably be determined by means of computer programs known in the art such as GAP provided in the GCG program package (Needleman S B & Wunsch C D; *J. Mol. Biol.* 1970 48 443–453). Using GAP with the following settings for DNA sequence comparison: GAP creation penalty of 5.0 and GAP extension penalty of 0.3, the coding region of the DNA sequence exhibits a degree of identity preferably of at least 70%, in particular at least 80%, at least 85%, at least 90%, or even at least 95% to the coding region of the xylanase encoding part of the DNA sequence shown in SEQ ID NO: 1, or to the DNA sequence obtainable from the plasmid in the strain *Saccharomyces cerevisiae* DSM 10133.

The hybridization referred to in (ii) above is intended to indicate that the analogous DNA sequence hybridizes to the same oligonucleotide probe as the DNA sequence encoding the xylanase component under certain specified conditions which are described in detail in the Materials and Methods section, below. The probe to be used may conveniently be constructed on the basis of the xylanase encoding part of the DNA sequence SEQ ID No. 1, or a sub-sequence thereof encoding at least 6–7 amino acids of the enzyme, or on the basis of the deduced amino acid sequence shown in SEQ ID NO 2. In the latter case the probe is prepared from an amino acid subsequence corresponding to a high number of low degenerated codons.

Normally, the analogous DNA sequence is highly homologous to the DNA sequence such as at least 70% homologous to sequence shown in SEQ ID NO: 1 encoding a xylanase component of the invention, preferably at least 80%, in particular at least 85%, at least 90%, or even at least 95% homologous to the sequence shown in SEQ ID NO: 1.

The degree of homology referred to in (iii) above is determined as the degree of identity between the two sequences indicating a derivation of the first sequence from the second. The homology may suitably be determined by means of computer programs known in the art, e.g. GAP provided in the GCG program package (Needleman S B & Wunsch C D; *J. Mol. Biol.*, 1970 48 443–453). Using GAP with the following settings for polypeptide sequence comparison: GAP creation penalty of 3.0 and GAP extension penalty of 0.1, the polypeptide encoded by an analogous DNA sequence exhibits a degree of identity preferably of at least 70%, in particular at least 80%, at least 85%, at least 90%, or even at least 95%, to the enzyme encoded by a DNA construct comprising the xylanase encoding part of the DNA sequence shown in SEQ ID NO: 1 or the DNA sequence obtainable from the plasmid in the strain *Saccharomyces cerevisiae* DSM 10133.

According to the method described in the above, the DNA homology of the xylanase of the invention against most prior art xylanases was determined using the computer program GAP. The xylanase of the invention showed only 63% DNA homology to the xylanase I from *Trichoderma reesei* (Torronen A et al., *Biotechnology* 1992 10 11 1461–1465), and 63% DNA homology to xylanase I from *Cochliobolus carbonum* (Apel P C et al.; *Mol. Plant Microb. Interact.* 1993 6 467–473).

The term "derived from" in connection with property (iv) above is intended not only to indicate a xylanase component produced by the strain *Thermomyces lanuginosus,* DSM 4109, but also a xylanase component encoded by a DNA sequence isolated from this strain and produced in a host cell transformed with said DNA sequence. The immunological reactivity may be determined by the method described in the Materials and Methods section below.

Feed Enhancing Enzymes

In a further preferred embodiment, the feed additive of the invention may comprise additional feed enhancing enzymes.

In the context of this invention feed enhancing enzymes comprises but are not limited to α-galactosidases, β-galactosidases, in particular lactases, phytases, β-glucanases, in particular endo-β-1,4-glucanases and endo-β-1,3(4)-glucanases, xylanases, xylosidases, galactanases, in particular arabinogalactan endo-1,4-β-galactosidases and arabinogalactan endo-1,3β-galactosidases, endoglucanases, in particular endo-1,2β-glucanase, endo-1,3α-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases and lipolytic enzymes such as lipases and cutinases.

Microbial Sources

The present invention relates to an animal feed additive, which additive comprises a xylanase derived from a strain belonging to the group of thermophilic fungi, i.e. *Thermomyces,* or a related genus.

The genus *Thermomyces,* embracing several species [Appinis & Eggins; 1966], more specifically the species *Thermomyces lanuginosus* (Syn. *Humicola lanuginosa*), has classically been associated the group of thermophillic fungi [Cooney & Emerson; 1964]. Several of the genera belonging to this group, e.g. species of *Humicola, Thermoascus, Chaetomium, Mucor, Talaromyces, Malbranchea, Myceliophthora, Thielavia,* [Cooney & Emerson; 1964], has been experienced to be very potent enzyme producers. Also *Byssochlamus* and *Paecilomyces* have been associated to this group.

The taxonomic affiliation of *Thermomyces* has been generally recognized as uncertain. However, the National Institute of Health database Entrez (updated January 1996) classifies *Thermomyces* as a mitosporic *Pyrenomycete* (viz a Pyrenomycete which is only incompletely characterized, not giving sufficient information as to associate it to a neither a specific order nor even a specific family).

Most recent molecular studies have attempted an elucidation of the 18S-RNA sequence of *Thermomyces* in order to use this information to further clarify the phylogenetic relationship of this genus. Tentative interpretation of the available data suggests that *Thermomyces* is closer affiliated to the fungi grouped under the *Plectomycetes,* in particular under *Erotiales.* Through homology search in data base the sequence of 18S-RNA of *Byssochlamus* is the sequence most related to the described sequence of *Thermomyces lanuginosus* (Novo Nordisk 1996, unpublished data). If case studies of more isolates belonging to the genus *Thermomyces* are supporting the preliminary findings, it could support a transfer of the genus *Thermomyces* to the order of *Plectomycetes.* Accordingly, the present invention also relates to xylanase preparations derived from *Plectomycetes,* more particularly *Erotiales.*

A homology search with the xylanase of the invention against nucleotide and protein databases was performed. The homology search showed that the most related xylanases were xylanase I from *Trichoderma reesei* and xylanase I from *Cochliobolus carbonum.* Both xylanases belongs to family 11 of glycosyl hydrolases (Henrissat B; *Biochem. J.* 1991 280 309–316), which indicates that the xylanase of the invention also belongs to this family.

Several samples of *Thermomyces lanuginosus* have been deposited and are publicly available from International depository authorities recognized under the Budapest treaty, e.g. American Type Culture Collection (ATCC), 12301 Parklawn Drive, Rockville, Md. 20852, USA. A strain of *Thermomyces lanuginosus* has been deposited according to the Budapest Treaty on the International Recognition of the Deposit of Microorganisms for the Purposes of Patent Procedure at Deutsche Sammlung von Mikroorganismen und Cellkulturen (DSM), Mascheroder Weg 1*b*, DE-3300 Braunschweig, Germany, on 4 May 1987, and allotted the Accession No. DSM 4109.

A strain of *Saccharomyces cerevisiae* DSM 10133, containing plasmid DNA comprising the full length DNA sequence presented as SEQ ID NO: 1, encoding the endoglucanase of the invention, in the yeast vector pYES 2.0, was deposited according to the Budapest Treaty on the International Recognition of the Deposit of Microorganisms for the Purposes of Patent Procedure at Deutsche Sammlung von Mikroorganismen und Cellkulturen (DSM), Mascheroder Weg 1*b*, DE-3300 Braunschweig, Germany, on 19 July 1995, and allotted the Accession No. DSM 10133.

DNA Constructs

In yet another aspect, the invention provides a DNA construct comprising a DNA sequence encoding a xylanase component, which DNA sequence comprises:

a) the xylanase encoding part of the DNA sequence presented as SEQ ID NO: 1, or the DNA sequence obtainable from the plasmid in the strain *Saccharomyces cerevisiae* DSM 10133; or b) a DNA sequence analogue to the xylanase encoding part of the DNA sequence presented as SEQ ID NO: 1, or to the DNA sequence obtainable from the plasmid in the strain *Saccharomyces cerevisiae* DSM 10133, which analog DNA sequence either i) is homologous to the xylanase encoding part of the DNA sequence presented as SEQ ID NO: 1, or to the DNA sequence obtainable from the plasmid in the strain *Saccharomyces cerevisiae* DSM 10133; or ii) hybridizes with the same oligonucleotide probe as the xylanase encoding part of the DNA sequence presented as SEQ ID NO: 1, or with the DNA sequence obtainable from the plasmid in the strain *Saccharomyces cerevisiae* DSM 10133; or iii) encodes a polypeptide which is at least 70% homologous to the polypeptide encoded by the DNA sequence presented as SEQ ID NO: 1, or to the DNA sequence obtainable from the plasmid in the strain *Saccharomyces cerevisiae* DSM 10133; or iv) encodes a polypeptide which is immunologically reactive with an antibody raised against the purified xylanase derived from the strain *Thermomyces lanuginosus*, DSM 4109, or encoded by the DNA sequence presented as SEQ ID NO: 1, or the DNA sequence obtainable from the plasmid in the strain *Saccharomyces cerevisiae* DSM 10133.

As defined herein the term "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding the xylanase of interest. The construct may optionally contain other nucleic acid segments.

The DNA construct of the invention encoding the xylanolytic enzyme may suitably be of genomic or cDNA origin, for instance obtained by preparing a genomic or cDNA library and screening for DNA sequences coding for all or part of the xylanolytic enzyme by hybridization using synthetic oligonucleotide probes in accordance with standard techniques (cf. e.g. Sambrook et al., *Molecular Cloning. A Laboratory Manual,* Cold Spring Harbor, N.Y., 1989).

The nucleic acid construct of the invention encoding the xylanolytic may also be prepared synthetically by established standard methods, e.g. the phosphoamidite method described by Beaucage and Caruthers, *Tetrahedron Letters* 1981 22 1859–1869, or the method described by Matthes et al., *EMBO Journal* 1984 3 801–805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or by Saiki et al., *Science* 1988 239 487–491.

The DNA sequence encoding a xylanase component may be derived from a strain of *Byssochlamus, Chaetomium, Humicola, Malbranchea, Mucor, Myceliophthora, Paecilomyces, Talaromyces, Thermoascus,* or *Thielavia.*

In a preferred embodiment, the DNA sequence encoding the xylanase component is derived from a strain of *Thermomyces,* more particularly a strain of *Thermomyces lanuginosus.* In a most preferred embodiment, the DNA sequence is derived from, or produced on the basis of, a DNA library of *Thermomyces lanuginosus,* DSM 4109, or a mutant or a variant thereof.

The DNA sequence encoding the xylanolytic enzyme may be isolated by conventional methods, which methods may typically involve, cloning, in a suitable vector, a cDNA library, e.g. from the strain *Thermomyces lanuginosus,* DSM 4109, or from the plasmid in the strain *Saccharomyces cerevisiae* DSM 10133, transforming a suitable host cell with said vector, culturing the host cell under conditions suitable to express the desired xylanolytic enzyme encoded by one or more clones in the cDNA library, screening for positive clones by determining any xylanolytic activity of the enzyme produced by such clones, and isolating the DNA encoding the desired xylanolytic enzyme from such clones.

A general method has been disclosed in WO 93/11249, the contents of which are hereby incorporated by reference. A more detailed description of the screening method is given in Example 1 below.

The DNA sequence encoding a xylanase component may for instance be isolated by screening a cDNA library of a strain of *Thermomyces lanuginosus* and selecting for clones expressing the xylanolytic enzyme (e.g. as defined by the ability of the enzyme to hydrolyse 1,4β-xylosidic linkages in 1,4-βoxylans). The appropriate DNA sequence may then be isolated from the clone by standard procedures, e.g. as described in Example 1.

In a currently preferred embodiment, the nucleic acid construct of the invention comprises the xylanase encoding part of the DNA sequence shown in SEQ ID NO: 1, on any subsequence thereof, but which differ from the DNA sequence shown in SEQ ID NO: 1 by virtue of the degeneracy of the genetic code. The invention further encompasses nucleic acid sequences which hybridize to a nucleic acid molecule (either genomic, synthetic or cDNA or RNA) encoding the amino acid sequence shown in SEQ ID NO: 2, or any subsequence thereof, under the conditions described below.

Recombinant Expression Vectors

In another aspect, the invention provides a recombinant expression vector comprising the DNA construct of the invention.

The recombinant expression vector of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector of the invention, the DNA sequence encoding the xylanolytic enzyme preferably is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the xylanolytic enzyme.

Thus, in the expression vector of the invention, the DNA sequence encoding the xylanolytic enzyme should be operably connected to a suitable promoter and terminator sequence.

The promoter may be any DNA sequence which shows transcriptional activity in the host cell of choice and may be derived from genes encoding proteins either homologous or heterologous to the host cell.

Examples of suitable promoters for directing the transcription of the DNA encoding the xylanolytic enzyme of the invention in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylanase or xylosidase gene, or by the phage Lambda $P_R$ or $P_L$ promoters or the *E. coli* lac, trp or tac promoters.

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al., eds.), Plenum Press, New York, 1982), or the *TPI*1 (U.S. Pat. No. 4,599,311) or *ADH*2-4c (Russell et al., *Nature* 304 (1983), 652–654) promoters.

Examples of suitable promoters for use in filamentous fungus host cells are, for instance, the *ADH*3 promoter (McKnight et al., *The EMBO J.* 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase. Preferred are the TAKA-amylase and gluA promoters.

The expression vector of the invention may further comprise a DNA sequence enabling the vector to replicate in the host cell in question. The expression vector may also comprise a selectable marker, e.g. a gene the product of which complements a defect in the host cell, such as the gene coding for dihydrofolate reductase (DHFR) or the *Schizosaccharomyces pombe* TPI gene (described by Russell P R, *Gene* 1985 40 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

To direct the xylanolytic enzyme into the secretory pathway of the host cells, a secretory signal sequence (also known as a leader sequence, prepro sequence or pre sequence) may be provided in the expression vector. The secretory signal sequence is joined to the DNA sequence encoding the xylanolytic enzyme in the correct reading frame. Secretory signal sequences are commonly positioned 5' to the DNA sequence encoding the xylanolytic enzyme. The secretory signal sequence may be that normally associated with the xylanolytic enzyme or may be from a gene encoding another secreted protein.

In a preferred embodiment, the expression vector of the invention may comprise a secretory signal sequence substantially identical to the secretory signal encoding sequence of the *Bacillus licheniformis* α-amylase gene, e.g. as described in WO 86/05812.

Also, measures for amplification of the expression may be taken, e.g. by tandem amplification techniques, involving single or double crossing-over, or by multicopy techniques, e.g. as described in U.S. Pat. No. 4,959,316 or WO 91/09129. Alternatively the expression vector may include a temperature sensitive origin of replication, e.g. as described in EP 283,075.

Procedures for ligating DNA sequences encoding the xylanolytic enzyme, the promoter and optionally the terminator and/or secretory signal sequence, respectively, and to insert them into suitable vectors containing the information necessary for replication, are well known to persons skilled in the art (cf., for instance, Sambrook et al., *Molecular Cloning. A Laboratory Manual*, Cold Spring Harbor, N.Y., 1989).

Host Cells

In yet another aspect the invention provides a host cell comprising the DNA construct of the invention and/or the recombinant expression vector of the invention.

The DNA construct of the invention may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. In this context, the term "homologous" is intended to include a cDNA sequence encoding a xylanolytic enzyme native to the host organism in question. The term "heterologous" is intended to include a DNA sequence not expressed by the host cell in nature. Thus, the DNA sequence may be from another organism, or it may be a synthetic sequence.

The host cell of the invention, into which the DNA construct or the recombinant expression vector of the invention is to be introduced, may be any cell which is capable of producing the xylanolytic enzyme and includes bacteria, yeast, fungi and higher eukaryotic cells.

Examples of bacterial host cells which, on cultivation, are capable of producing the xylanolytic enzyme of the invention are grampositive bacteria such as strains of *Bacillus*, in particular a strain of *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megatherium, Bacillus pumilus, Bacillus thuringiensis* or *Bacillus agaradherens*, or strains of *Streptomyces*, in particular a strain of *Streptomyces lividans* or *Streptomyces murinus*, or gramnegative bacteria such as *Echerichia coli*. The transformation of the bacteria may be effected by protoplast transformation or by using competent cells in a manner known per se (cf. Sambrook et al., *Molecular Cloning. A Laboratory Manual*, Cold Spring Harbor, N.Y., 1989).

When expressing the xylanolytic enzyme in bacteria such as *Escherichia coli*, the xylanase may be retained in the cytoplasm, typically as insoluble granules (known as inclusion bodies), or may be directed to the periplasmic space by a bacterial secretion sequence. In the former case, the cells are lysed and the granules are recovered and denatured after which the xylanolytic enzyme is refolded by diluting the denaturing agent. In the latter case, the xylanolytic enzyme may be recovered from the periplasmic space by disrupting the cells, e.g. by sonication or osmotic shock, to release the contents of the periplasmic space and recovering the xylanolytic enzyme.

Examples of suitable yeasts cells include cells of *Saccharomyces* sp., in particular strains of *Saccharomyces cerevisiae, Saccharomyces kluyveri*, and *Saccharomyces uvarum*, cells of *Schizosaccharomyces* sp., such as *Schizosaccharomyces pombe*, cells of *Kluyveromyces*, such as *Kluyveromyces lactis*, cells of *Hansenula*, e.g. *Hansenula polymorpha*, cells of *Pichia*, e.g. *Pichia pastoris* (cf. Gleeson et al., *J. Gen. Microbiol.* 132, 1986, pp. 3459–3465; U.S. Pat. No. 4,882,279), and cells of *Yarrowia* sp. such as

*Yarrowia lipolytica*. Methods for transforming yeast cells with heterologous DNA and producing heterologous polypeptides there from are described, e.g. in U.S. Pat. No. 4,599,311, U.S. Pat. No. 4,931,373, U.S. Pat. No. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the xylanolytic enzyme of the invention may be preceded by a signal sequence and optionally a leader sequence, e.g. as described above.

Examples of other fungal cells are cells of filamentous fungi, e.g. *Aspergillus* sp., in particular strains of *Aspergillus japonicus, Aspergillus oryzae, Aspergillus nidulans* or *Aspergillus niger, Neurospora* sp., *Fusarium* sp., in particular strains of *Fusarium oxysporum* or *Fusarium graminearum*, or *Trichoderma* sp. Fungal cells may be transformed by a process involving protoplast formation and transformation of the protoplasts followed by regeneration of the cell wall in a manner known per se. The use of *Aspergillus* sp. for the expression of proteins have been described in e.g., EP 272,277 and EP 230,023. The transformation of *F. oxysporum* may, for instance, be carried out as described by Malardier et al., *Gene* 1989 78 147–156. The use of *Aspergillus* as a host microorganism is described in e.g. EP 238 023, the contents of which are hereby incorporated by reference.

In a preferred embodiment, the host cell is a strain of *Aspergillus oryzae*.

Methods of Producing a Monocomponent Preparation

In a still further aspect, the present invention provides a method of producing the xylanolytic enzyme of the invention, wherein a suitable host cell, which has been transformed with a DNA sequence encoding the xylanolytic enzyme, is cultured under conditions permitting the production of the enzyme, and the resulting enzyme is recovered from the culture.

In a further aspect, the present invention relates to a method of producing a monocomponent xylanase preparation, wherein a suitable host cell transformed with a DNA sequence encoding the enzyme is cultured under conditions permitting the production of the xylanase component, followed by recovery of the xylanase component from the culture.

In a preferred embodiment the DNA sequence encoding the enzyme is a DNA construct obtained as described above.

In another preferred embodiment, the DNA construct is combined with an appropriate expression signal in an expression vector as described above.

In a further preferred embodiment, the host cell is one described above.

The medium used for culturing the transformed host cells may be any conventional medium suitable for growing the host cells in question. The expressed xylanolytic enzyme may conveniently be secreted into the culture medium and may be recovered there from by purification procedures. Well-known purification procedures include separating the cells from the medium by centrifugation or filtration, precipitating proteinaceous components of the medium by means of a salt such as ammonium sulphate, and chromatographic methods such as e.g. ion exchange chromatography, affinity chromatography.

EXAMPLES

The invention is further illustrated with reference to the following examples which are not intended to be in any way limiting to the scope of the invention as claimed.

MATERIALS AND METHODS

Donor Organism mRNA was isolated from *Thermomyces lanuginosus*, DSM 4109, grown in a xylan containing fermentation medium with agitation to ensure sufficient aeration. Mycelia were harvested after 3–5 days of growth, immediately frozen in liquid nitrogen and stored at $-80°$ C.

Yeast Strains

The *Saccharomyces cerevisiae* strain used below is JG169 (MAT$\alpha$; ura 3–52; leu 2–3, 112; his 3-D200; pep 4–113; prc1::HIS3; prb1:: LEU2; cir+).

Plasmids

For expression the commercially available yeast plasmid pYES 2.0 (Invitrogen) was used.

The *Aspergillus* expression vector pHD414 is a derivative of the plasmid p775, which was described in EP 238 023. The construction of pHD414 is further described in WO 93/11249.

Extraction of Total RNA

Extraction of total RNA was performed with guanidinium thiocyanate followed by ultracentrifugation through a 5.7 M CsCl cushion, and isolation of poly(A)+RNA by oligo(dT)-cellulose affinity chromatography using the procedures described in WO 93/11249.

cDNA Synthesis and Modification

Double-stranded cDNA was synthesized from 5 $\mu$g of poly(A)+RNA by the RNase H method (Gubler U, Hoffman B J, *Gene* 1983 25 263–269; Sambrook et al., *Molecular Cloning: A Laboratory Manual,* Cold Spring Harbor Lab., Cold Spring Harbor, N.Y., 1989) using the hair-pin modification. The procedure is further described in WO 93/11249.

After having been treated with mung bean nuclease, the ds cDNA was made blunt-ended with T4 DNA polymerase (Invitrogen) and the cDNA was ligated to non-palindromic BstX I adaptors (1 $\mu$g/$\mu$l, Invitrogen) in accordance with the manufacturers instructions.

Construction of cDNA Libraries

The adapted, ds cDNA was recovered by centrifugation, washed in 70% EtOH and resuspended in 25 ml $H_2O$. Prior to large-scale library ligation, four test ligations were carried out in 10 $\mu$l of ligation buffer (same as above), each containing 1 $\mu$l ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either pYES 2.0 vector, Invitrogen, or yHD13).

Using the optimal conditions, a large-scale ligation was set up in 40 $\mu$l of ligation buffer. One $\mu$l aliquot were transformed into electrocompetent *E. coli* 1061 cells, and the transformed cells were titered and the library plated on LB+ampicillin plates with 5000–7000 c.f.u./plate. To each plate was added 3 ml of medium. The bacteria were scraped off, 1 ml glycerol was added and stored at $-80°$ C. as pools. The remaining 2 ml were used for DNA isolation. For further details on this method, reference is made to WO 94/14952.

Construction of Yeast Libraries

To ensure that all the bacterial clones were tested in yeast, a number of yeast transformants 5 times larger than the number of bacterial clones in the original pools was set as the limit.

One $\mu$l aliquot of purified plasmid DNA (100 ng/$\mu$l) from individual pools were electrophorated (200$\Omega$, 1.5 kV, 25 $\mu$F) into 40 $\mu$l competent *Saccharomyces cerevisiae* JG169 cells ($OD_{600}$=1.5 in 500 ml YPD, washed twice in cold DIW, once in cold 1M sorbitol, resuspended in 0.5 ml 1M sorbitol (Becker D M, Guarante L, *Methods Enzymol.* 1991 194 182–187). After addition of 1 ml 1M cold sorbitol, 80 $\mu$l aliquot were plated on SC+glucose–uracil to give 250–400 c.f.u./plate and incubated at 30° C. for 3–5 days.

Identification of Positive Colonies

After 3–5 days of growth, the agar plates were replica plated onto SC-Uracil plates containing 0.2% Azurin-cross-linked birch xylan (AZCL™ birch xylan, Megazyme™, Australia), and 2% galactose, followed by incubation for 2–4 days at 30° C. for detection of xylanolytic activity. After incubation xylanolytic enzyme-positive colonies were identified as colonies with a blue halo around.

Cells from enzyme-positive colonies were spread for single colony isolation on agar, and an enzyme-producing single colony was selected for each of the xylanolytic enzyme-producing colonies identified.

Characterization of Positive Clones

The positive clones were obtained as single colonies. Plasmid DNA was isolated from a cell culture prepared from the two positive yeast colonies. Plasmid DNA was introduced (transformed) into *E. coli*, isolated and characterized individually by sequencing the 5'-end of each cDNA clone using the chain-termination method (Sanger et al., *Proc. Natl. Acad. Sci. U.S.A.* 1977 74 5463–5467), and the Sequenase™ System (United States Biochemical).

Isolation of a cDNA Gene for Expression in *Aspergillus*

One or more xylanolytic enzyme-producing yeast colonies were inoculated into 20 ml YNB-1 broth in a 50 ml glass test tube. The tube was shaken for 2 days at 30° C. The cells were harvested by centrifugation for 10 min. at 3000 rpm.

DNA, isolated according to WO 94/14952, was dissolved in 50 μl water. Aliquot of the DNA were transformed with *E. Coli* as described in WO 94/14952. Plasmid DNA was isolated from *E. Coli* using standard procedures, and analyzed by restriction enzyme analysis. The cDNA insert was excised using appropriate restriction enzymes and ligated into an *Aspergillus* expression vector.

Transformation of *Aspergillus oryzae* or *Aspergillus niger* General Procedure 100 ml of YPD (Sherman et al., *Methods in Yeast Genetics*, Cold Spring Harbor Laboratory, 1981) is inoculated with spores of *Aspergillus oryzae* or *Aspergillus niger* and incubated with shaking at 37° C. for about 2 days. The mycelium is harvested by filtration and washed with 200 ml of 0.6 M MgSO$_4$. The mycelium is suspended in 15 ml of 1.2 M MgSO$_4$ and 10 mM NaH$_2$PO$_4$, pH 5.8. The suspension is cooled on ice and 1 ml of buffer containing 120 mg of Novozym™ 234, batch 1687 is added. After 5 minutes 1 ml of 12 mg/ml BSA (Sigma, type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH 7.0. Centrifugation is performed for 15 minutes at 100 g and the protoplasts are collected from the top of the MgSO$_4$ cushion. 2 volumes of STC (1.2M sorbitol, 10 mM Tris-HCl, pH 7.5, 10 mM CaCl$_2$) are added to the protoplast suspension and the mixture is centrifuged for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an *Aspergillus nidulans* amdS gene carrying plasmid). The mixture is left at room temperature for 25 minutes. 0.2 ml of 60% PEG 4000 (BDH 29576). 10 mM CaCl$_2$ and 10 mM Tris-HCl, pH 7.5, is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove, *Biochem. Biophys. Acta* 1966 113 51–56) containing 1.0M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of Aspergillus oryzae Transformants

Each of the transformants were inoculated in 10 ml of YPM (cf. below) and propagated. After 2–5 days of incubation at 30° C., the supernatant was removed. The xylanolytic activity was identified by applying 10 μl supernatant to 4 mm diameter holes punched out in agar plates containing 0.2% AZCL™ birch xylan (Megazyme™, Australia). Xylanolytic activity is then identified as a blue halo.

Hybridization Conditions

Suitable hybridization conditions for determining hybridization between an oligonucleotide probe and an "analogous" DNA sequence of the invention may be defined as described below. A suitable oligonucleotide probe to be used in the hybridization may be prepared on the basis of the xylanase encoding part of the DNA sequence shown in SEQ ID NO: 1, or any sub-sequence thereof, or on the basis of the deduced amino sequence shown in SEQ ID NO: 2. An example of a suitable probe, is the DNA sequence corresponding to the xylanase encoding part of SEQ ID NO: 1, i.e. nucleotides at positions 31–705 in SEQ ID NO: 1.

A filter containing the DNA fragments to hybridize is subjected to presoaking in 5x SSC, and prehybridized for 1 hour at about 50° C. in a solution of 5x SSC, 5x Denhardt's solution, 50 mM sodium phosphate, pH 6.8, and 50 μg of denatured sonicated calf thymus DNA. After hybridization for 18 hours at ~45° C. in the same solution supplemented with 50 μCi 32-P-dCTP labelled probe, the product is washed three times in 2x SSC, 0.2% SDS, for 30 minutes at preferably no more than 55° C., in particular no more than 60° C., no more than 65° C., no more than 70° C., no more than 75° C., preferably no more than 80° C.

Molecules to which under these conditions the oligonucleotide probe hybridizes, may be detected using an x-ray film.

Immunological Cross-reactivity

Antibodies to be used in determining immunological cross-reactivity may be prepared by use of a purified xylanolytic enzyme. More specifically, antiserum against the enzyme of the invention may be raised by immunizing rabbits (or other rodents) according to the procedure described by Axelsen et al.; *A Manual of Quantitative Immunoelectrophoresis*, Blackwell Scientific Publications, 1973, (in particular Chapter 23), or by Johnstone and Thorpe; *Immunochemistry in Practice*, Blackwell Scientific Publications, 1982 (in particular pp. 27–31).

Purified immunoglobulins may be obtained from the antisera, for example by salt precipitation (($NH_4$)$_2$SO$_4$), followed by dialysis and ion exchange chromatography, e.g. on DEAE-Sephadex. Immunochemical characterization of proteins may be done either by Outcherlony double-diffusion analysis (Ouchterlony O; *Handbook of Experimental Immunology* (D. M. Weir, Ed.), Blackwell Scientific Publications, 1967, pp. 655–706; or Roitt I; *Essential Immunology*, Blackwell Scientific Publications, 1984, pp. 145–147), by crossed immunoelectrophoresis (Axelsen et al., supra, Chapters 3 and 4), or by rocket immunoelectrophoresis (Axelsen et al., supra, Chapter 2).

Media

YPM media: 10 g yeast extract, 20 g peptone, $H_2O$ to 810 ml. 90 ml 20% maltodextrin, autoclaved and sterile filtered, is added.

YPD media: 10 g yeast extract, 20 g peptone, $H_2O$ to 810 ml. 90 ml 20% glucose, autoclaved and sterile filtered, is added.

10×Basal salt media: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto™). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

Xylanolytic Activity

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue colour in the supernatant (as determined spectrophotometrically at 585 nm) is proportional to the xylanase activity, and the xylanase units are then determined relatively to an enzyme standard at standard reaction conditions, i.e. at 50.0° C., pH 6.0, and 30 minutes reaction time.

A folder AF 293.6/1 describing this analytical method in more detail is available upon request to Novo Nordisk A/S, Denmark, which folder is hereby included by reference.

EXAMPLE 1

Isolation of the Gene

A library from *Thermomyces lanuginosus* consisting of approx. 1.5×106 individual clones in 150 pools was constructed. DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates.

One set of plates containing 0.1% AZCL™ xylan (Megazyme™, Australia) was then incubated for 3–5 days at 30° C. to detect for xylanase activity. Positive colonies were identified as colonies surrounded by a blue halo. Alternatively, one set of plates was then incubated for 3–5 days at 30° C. before over-layering with a xylan overlayer gel containing 0.1% AZCL™ xylan and 1% agarose in a buffer with an appropriate pH. After incubation for 1–2 days at 30° C., positive colonies were identified as colonies surrounded by a blue halo.

Cells from enzyme-positive colonies were spread for single colony isolation on agar, and an enzyme-producing single colony was selected for each of the xylanase-producing colonies identified.

Characterization of Positive Clones

The positive clones were obtained as single colonies. cDNA inserts were amplified directly from the yeast colony using biotinylated polylinker primers, purified by magnetic beads (Dynabead™ M-280, Dynal) system and characterized individually by sequencing the 5'-end of each cDNA clone using the chain-termination method (Sanger F, Nicklen S & Coulson A R; *Proc. Natl. Acad. Sci. U.S.A.* 1977 74 5463–5467) and the Sequenase™ System (United States Biochemical).

The DNA sequence is shown as SEQ ID NO: 1, which corresponds to the amino acid sequence presented as SEQ ID NO: 2.

Isolation of Yeast DNA

In order to avoid PCR errors in the gene to be cloned, the cDNA was isolated from the yeast plasmids by standard procedures, e.g. as described in Example 1 of WO 93/11249, which publication is hereby included by reference. The yeast DNA was dissolved in 50 μl water to a final concentration of approximately 100 μl/ml.

The DNA was transformed into *Escherichia coli* by standard procedures. Two *E. coli* colonies were isolated from each of the transformations and analyzed with the restriction enzymes HindIII and XbaI which excised the DNA insert. DNA from one of these clones was retransformed into yeast strain JG169.

The DNA sequences of several of the positive clones were partially determined. The DNA sequences of the xylanase of the invention is shown as SEQ ID NO: 1, which corresponds to the amino acid sequence presented as SEQ ID NO: 2.

EXAMPLE 2

Expression in *Aspergillus*

In order to express the gene in *Aspergillus*, cDNA is isolated from one of the above clones by digestion with HindIII/XbaI or other appropriate restriction enzymes, size fractionation on a gel and purification and subsequently ligated to pHD414, resulting in plasmid pA2XIT1. After amplification in *E. Coli*, the plasmid is transformed into a strain of *Aspergillus oryzae* according to the general procedure described in the Materials and Methods section above.

Test of *Aspergillus oryzae* Transformants

Each of the transformants were inoculated in 10 ml YPM medium. After 3–5 days of incubation at 30° C. and 250 rpm, the supernatant was removed. The xylanolytic activity was determined by applying 10 μl supernatant into 4 mm (diameter) holes punched in an agar plate containing 0.2% AZCL™ xylan (Megazyme™, Australia) in a buffer with an appropriate pH, and incubated overnight at 40° C. The xylanase activity was identified as described above. Some of the transformants had halos which were significantly larger than the *Aspergillus oryzae* background. This demonstrates efficient expression of xylanase in *Aspergillus oryzae*. The 8 transformants with the highest xylanase activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 $\mu$l of each supernatant was applied to 4 mm diameter holes punched out in a 0.1% AZCL™ xylan overlayer gel (25 ml in a 13 cm diameter petri dish). The xylanase activity was identified by the formation of a blue halo on incubation. Subsequently, the xylanase was fermented in a medium comprising maltodextrin as a carbon source, urea as a nitrogen source and yeast extract. The fermentation was performed by innoculating a shake flask culture of the *Aspergillus oryzae* host cells into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The cultivation was continued for 4 days, after which the enzymes could be recovered by centrifugation, ultrafiltration, clear filtration and germ filtration.

EXAMPLE 3

Purification Example

The culture supernatant from fermentation of *Aspergillus oryzae*, described in Example 2, expressing the recombinant enzyme is centrifugated and filtered through a 0.2 $\mu$m filter to remove the mycelia.

100 ml of the filtered supernatant is ultra-filtrated in a Filtron™ ultracette or Amicon™ ultrafiltration device with a 3 kDa membrane to achieve 10 fold concentration. This concentrate is diluted 100 times in 20 mM TRIS, pH 8.0, in two successive rounds of ultrafiltration in the same device. This ultrafiltration sample is loaded at 2 ml/min on a Pharmacia XK 26/20 Fast Flow Q Sepharose™ anion exchanger, equilibrated in 20 mM TRIS, pH 8.0.

After the sample has been applied, the column is washed with two column volumes 25 mM TRIS, pH 8.0, and bound proteins are eluted with a linear increasing NaCl gradient from 0 to 0.5M NaCl in 25 mM TRIS, pH 8.0. Fractions are collected and the xylanase activity in the fractions measured as described above.

Xylanase containing fractions are pooled and UF concentrated into 10 mM sodium citrate, pH 4.0. This material is loaded on a XK 16/20 Fast Flow S Sepharose™ column at 1.5 ml/min. The enzyme is eluted with a linear gradient from 0 to 0.4M NaCl and xylanase containing fractions pooled, concentrated and used for characterization and further experimentation as described below.

EXAMPLE 4

Enzyme Characterization

The xylanase obtained according to Example 3 was subjected to the following enzyme characterization.

SDS-PAGE Electrophoresis

SDS-PAGE (sodium dodecyl sulphate/polyacrylamide gel electrophoresis) was performed in a Mini-Leak 4 electrophoresis unit (Kem-En-Tec, Copenhagen) as a modified version of the Laemmli procedure (Laemmli UK; Nature 1970 227, 680–685; Christgau et al., 1991, J. Biol. Chem. 1991 266 p. 21157–212664].

A molecular weight (MW) of approximately 26 kDa was determined.

Isoelectric Focusing

Isoelectric focusing was carried out on Ampholine™ PAG plates, pH 3.5–9.5 (Pharmacia, Sweden) on a Multiphor™ electrophoresis unit according to the manufactures instructions. After electrophoresis, the gel was commassie stained according to standard protocols known in the art.

An isoelectric point (pI) of approximately 4.5 was determined.

pH and Temperature Optima

Enzymatic activities are measured by the release of blue colour from AZCL™ birch xylan (Megazyme, Australia).

0.5 ml 0.4% AZCL™ substrate suspension is mixed with 0.5 ml 0.1M citrate/phosphate buffer of optimal pH, and 10 $\mu$l of a suitably diluted enzyme solution is added. Incubations are carried out in Eppendorph Thermomixers for 15 minutes at 30° C., followed by heat inactivation for 20 minutes at 95° C. Enzyme incubations are carried out in triplicate. A blank is produced in which enzyme is added but inactivated immediately. After centrifugation, the absorbance of the supernatant is measured in microtiter plates at 620 nm and the blank is subtracted.

0.1M citrate/phosphate buffers of varying pH were used for determination of pH optimum. A 0.1M citrate/phosphate buffer, pH 5.5, for incubation at different temperatures for 15 minutes was used in order to determine the temperature optimum. The results are presented in FIGS. 1–2.

FIG. 1 shows the relative xylanolytic activity (%) determined at 30° C. in the range pH 2.5 to 9. It appears that the enzyme has a pH optimum in the range 4.5–7.5, more specifically the range 5.0–6.5, around pH 6.

Figure 2:
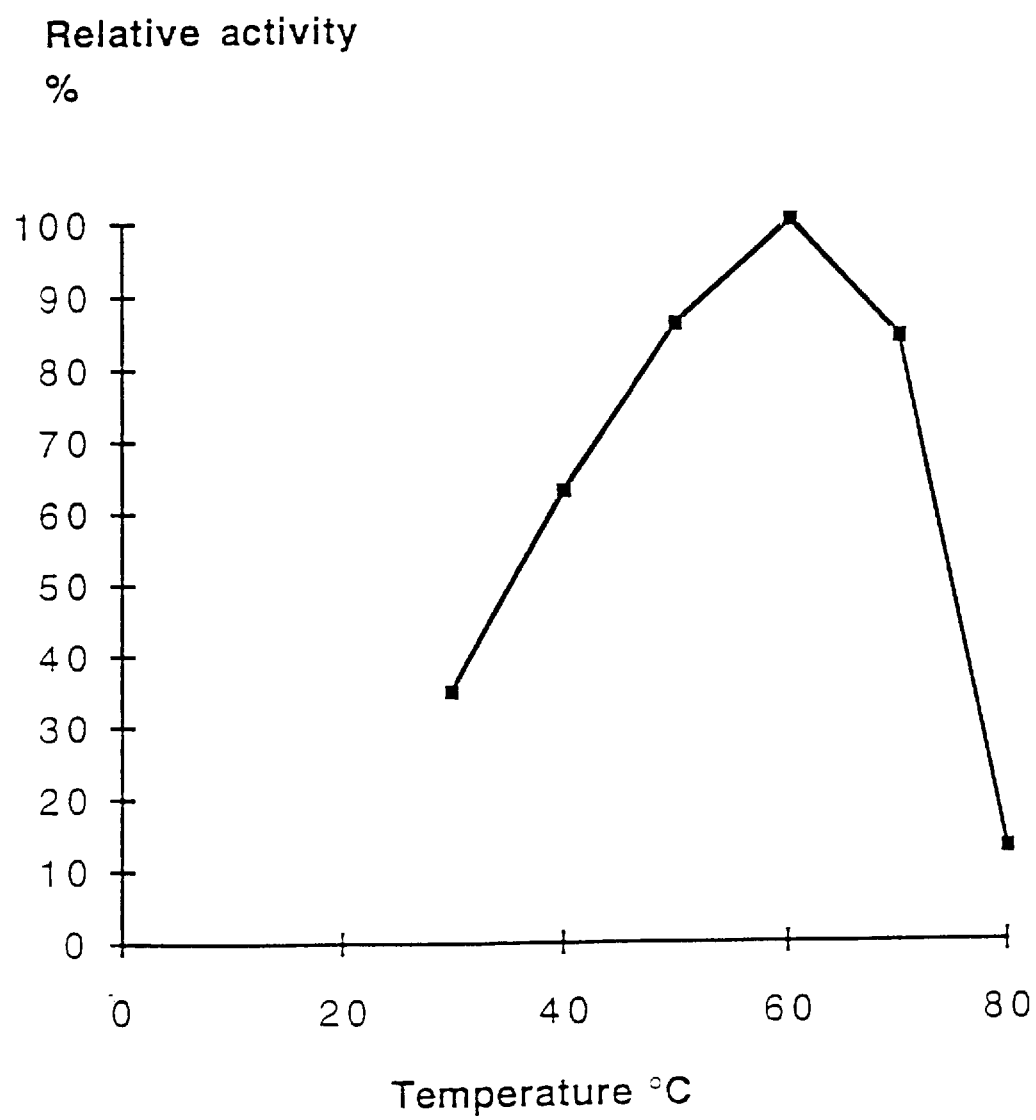
FIG. 2 shows the relative xylanolytic activity (%) of a monocomponent xylanase of the invention, determined at pH 5.5 in the range of from 30° to 80° C. It appears that the enzyme has a temperature optimum in the range 50°–70° C., around 60° C.

FIG. 2 shows the relative xylanolytic activity (%) determined at pH 5.5 in the range 30° to 80° C. It appears that the enzyme has a temperature optimum in the range 50°–70° C., around 60° C.

EXAMPLE 5

Thermal Stability Comparisons

In this example, the thermal stability of a monocomponent xylanase preparation obtained according to examples 1–3 was compared to that of the native *Thermomyces lanuginosus* xylanase preparation.

The native *Thermomyces lanuginosus* xylanase was prepared as described below.

The strain *Thermomyces lanuginosus* DSM 4109 was inoculated for 24 hours in 200 litre of YPG medium of the following composition (g/l):

| | |
|---|---|
| Yeast extract, 50% | 10 |
| Glucose | 5 |
| $KH_2PO_4$ | 3 |
| $Na_2HPO_4$, $2H_2O$ | 2 |
| $FeSO_4$ | 0.25 |

-continued

| | |
|---|---|
| MgSO$_4$, 7H$_2$O | 2 |
| Pluronic | 0.7 |
| pH adjusted to 6.0 | |

After inoculation, the inoculum was added to 2000 litre of the following medium (g/l) and fermented for additional 3 days:

| | |
|---|---|
| Sodium caseinat | 10 |
| Soy meal | 20 |
| Na$_2$HPO$_4$, 2H$_2$O | 2 |
| Xylan | 3 |
| Xylose | 500 |
| pH adjusted 7.5 | |

The cells were removed by centrifugation, the supernatant concentrated by ultrafiltration (using a 10,000MW cut off membrane), and the UF concentrate converted to a crude powder by freeze-drying.

The preparations were diluted with 100 mM citrate-phosphate buffer, pH 6.0, in order to bring the enzyme activity inside a linear analytical range when applied to the assay for enzymatic activity described below, The diluted samples were placed in a water bath in aliquots of 2 ml at temperatures of 60°, 65°, 70° and 75° C. A control was kept in ice water. Incubated samples were removed after 60 and placed in ice water.

As substrate remazol-xylan from beechwood was used (4-O-methyl-D-glucurono-D-xylan dyed with Remazol Brilliant Blue R, Fluka). The substrate was dissolved to make a 0.5% (w/v) solution with 100 mM citrate-phosphate buffer, pH 6.0.

Figure 3:
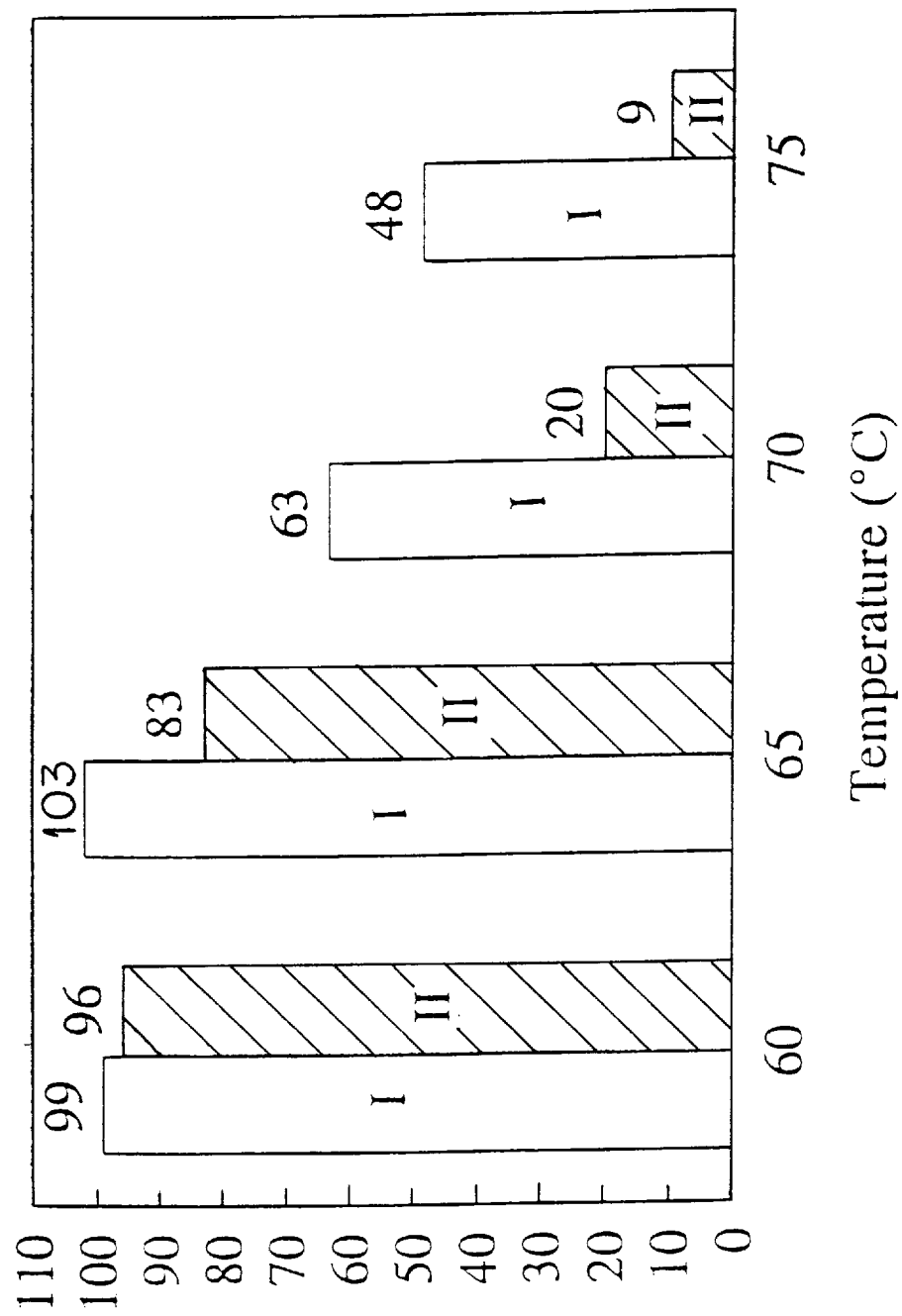
FIG. 3 shows the relative residual activity (%) of the monocomponent xylanase preparation of the invention (I) compared to that of the native *Thermomyces lanuginosus* xylanase preparation (II). Residual activity has been determined at pH 6.0 after incubation for 60 minutes at 60°, 65°, 70° and 75° C., respectively.

For determining residual enzyme activities, 0.9 ml substrate was added to four tubes (two main values and two blanks) and preheated in a water bath at 50° C. for 5 min. At t=0, 0.1 ml of enzyme sample was added to all tubes constituting the main values and mixed. After 60 minutes the incubation was terminated by the addition of 5 ml of ethanol reagent (a mixture of 150 ml 99.9% ethanol and 1 ml 2 N HCl), followed by 10 seconds of shaking on a Whirlimixer. To all tubes constituting blanks, 5 ml of ethanol reagent was first added, followed by the addition of 0.1 ml of enzyme sample and shaking for 10 seconds on a Whirlimixer. All tubes were allowed to stand for approx. 15 minutes at ambient temperature before being subjected to centrifugation at 4.000 rpm for 10 minutes. Finally, optical density was measured at 585 nm, and double determinations averaged and blanks subtracted. The relative residual enzymatic activity determined as a function of incubation temperature and time was calculated as percentage of the control value (control value defined as "100%"). The results are presented in FIG. 3.

On the figure, the residual activity of the monocomponent xylanase preparation of the invention (white bars) compared to that of the native Thermomyces lanuginosus xylanase preparation (crossed bars) is presented. Residual activity determined at pH 6.0 and after incubation at 60°, 65°, 70° and 75° C. for 30 and 60 minutes, respectively, is shown.

From the figure it appears that the xylanase component of the invention has a residual enzyme activity after incubation for 60 minutes at pH 6.0 and 60° C. of more than 96%, more specifically more than 97%, essentially 100%.

After incubation for 60 minutes at pH 6.0 and 65° C., the xylanase component of the invention has a residual enzyme activity of more than 83%, in particular more than 85%, more particularly more than 90%, essentially 100%.

After incubation for 60 minutes at pH 6.0 and 70° C., the xylanase component of the invention has a residual enzyme activity of more than 20%, in particular more than 30%, more particularly more than 40%, yet more particularly more than 50%, around 63%.

After incubation for 60 minutes at pH 6.0 and 75° C., the xylanase component of the invention has a residual enzyme activity of more than 9%, in particular more than 10%, more particularly more than 20%, yet more particularly more than 30%, around 48%.

From the figure it also appears that the monocomponent xylanase preparation of the invention shows a significantly improved thermal stability when compared to that of the native Thermomyces lanuginosus xylanase preparation. besides being an excellent feed enhancing enzyme, this unexpected improvement in thermal stability makes the monocomponent xylanase preparation of the invention particularly well suited for incorporation into animal feed additives. During the incorporation into animal feed additives, the thermal stability of the enzyme plays an important role in preventing microbial infection of the fodder.

EXAMPLE 6

Reduction of In Vitro Viscosity

Foregut digesta viscosity has been identified as a major nutritional constraint affecting digestibility of wheat and barley based broiler diets. A close correlation between the reduction of digesta viscosity results and improvements in chicken feed conversion efficiency have been found [cf. e.g. Graham H, Bedford M and Choct M; *Feedstuffs* 1993 65 (5) 14–15].

In this experiment, the wheat viscosity reduction obtained by use of (i) a recombinantly produced monocomponent Thermomyces lanuginosus xylanase preparation obtained according to examples 1–3, (ii) a native Thermomyces lanuginosus xylanase preparation obtained by cultivation as described in Example 5, and (iii) a commercially available multicomponent enzyme preparation obtained by cultivation of *Humicola insolens* (Bio-Feed Plus CT, a product of Novo Nordisk A/S, Denmark), respectively, is examined.

At t=0, 12 g of grounded dry wheat ("Statens Husdyrbrugsforsøg", Foulum, Denmark), 1 mm mesh, was mixed with 38 ml extraction buffer, 0.5M HCl-KCl, pH 1.5, and kept in at 40° C. under constant stirring. During incubation, the samples were covered with tinfoil. At t=89 minutes, pH was adjusted to 6.0 (±0.15). with 1M NaOH. At t=90 minutes, enzyme solution to a total of 40 ml was added.

The above enzyme preparations (i)–(iii) were diluted to yield a final enzyme concentration in the range 0.16 to 5.19 FXU/g wheat. All experiments were made in double and samples, i.e. solutions without any enzyme added, were always included in double.

After 30 minutes of incubation the samples were removed for viscosity determination. A Brookfield LVDV-III Viscometer with a small sample adapter and spindle no. SC4-31 was used, at 250 rpm corresponding to a shear rate of 85 s$^{-1}$. For each determination, approx. 13 ml of suspension were quickly poured into the small sample adapter, which was placed in the water jacket with constant water heating to 40° C. Three separate cP readings, each per 15 seconds, was made and the average value used.

In all cases the resulting data obtained with enzyme added were expressed as relative viscosity, i.e. relative to the viscosity measured in the control samples, which were defined as "1".

Figure 4:
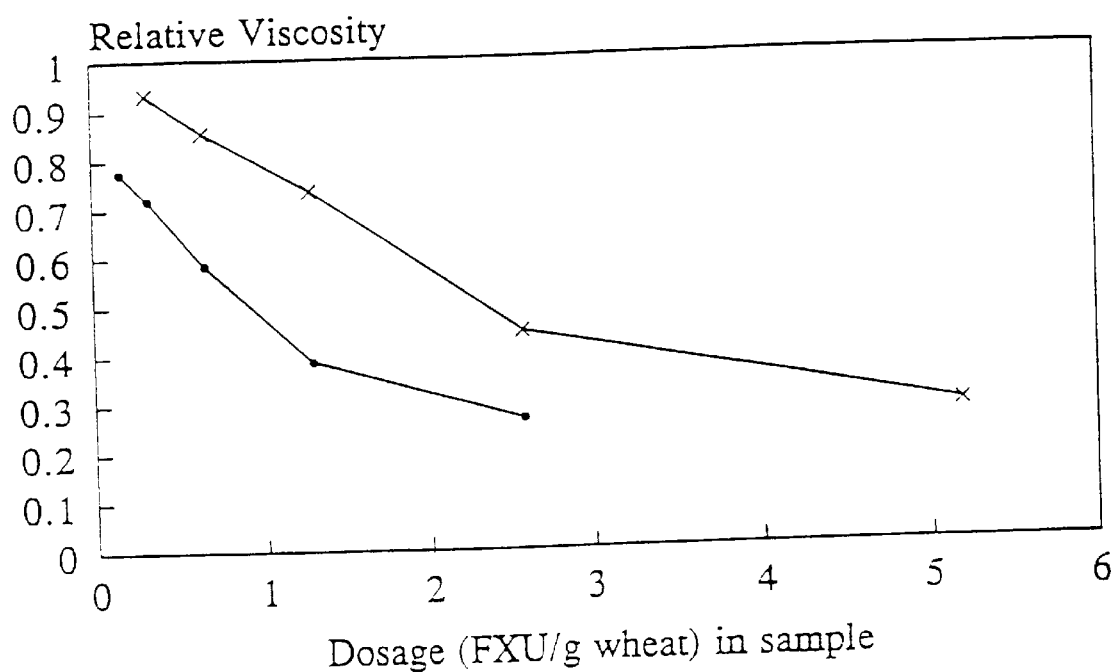
FIG. 4 shows the results of a comparison of wheat viscosity reduction efficiency between a native *Thermomyces lanuginosus* xylanase (●) and a multicomponent enzyme preparation obtained by cultivation of Humicola insolens (x) (dosage (FXU/g wheat) in sample)

In FIG. 4, the results of a comparison of wheat viscosity reduction efficiency between (ii) the native *Thermomyces lanuginosus* xylanase, dosed 0.16, 0.32, 0.65, 1.29 and 2.58 FXU/g wheat (●) and (iii) a multicomponent enzyme preparation obtained by cultivation of *Humicola insolens,* dosed 0.32, 0.65, 1.29, 2.58 and 5.19 FXU/g wheat (x) are shown. From the figure it appears that in comparison to (iii), a multicomponent enzyme preparation obtained by cultivation of *Humicola insolens,* the native *Thermomyces lanuginosus* xylanase (ii), significantly reduces the viscosity of a wheat suspension when calculated on a FXU basis.

Figure 5:
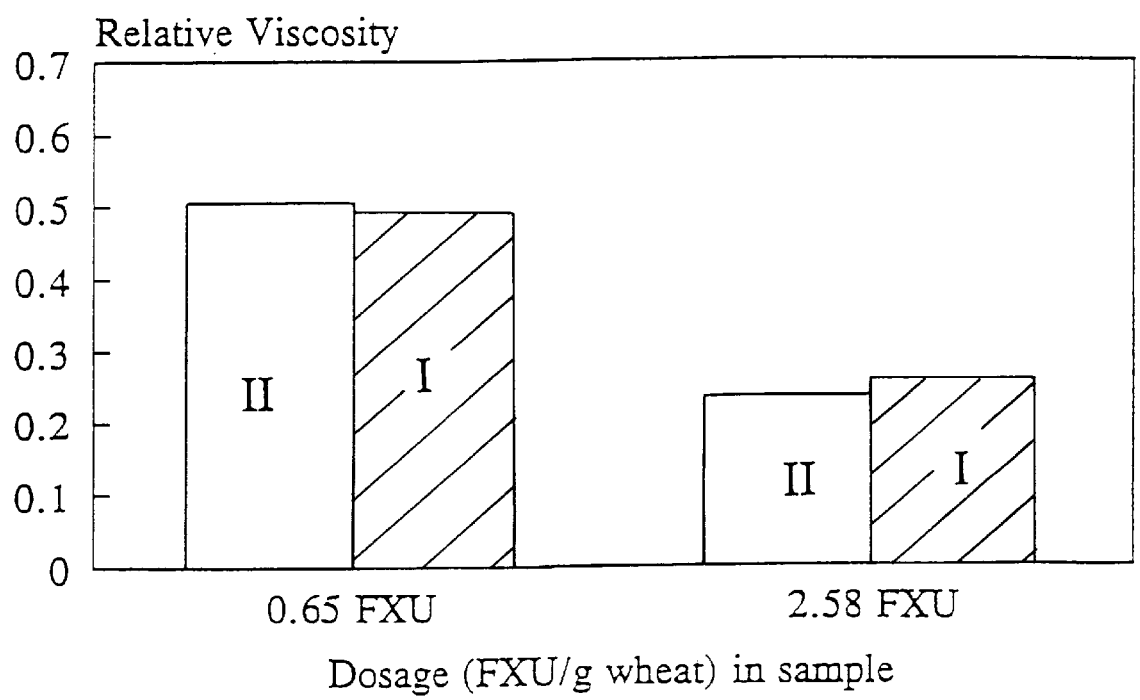
FIG. 5 shows the results of a comparison of wheat viscosity reduction efficiency between a recombinantly produced monocomponent *Thermomyces lanuginosus* xylanase (I) and a native *Thermomyces lanuginosus* xylanase (II) are shown (dosage (FXU/g wheat) in sample)

In addition, on FIG. 5, the results of a comparison of wheat viscosity reduction efficiency between (i) the recombinantly produced monocomponent *Thermomyces lanuginosus* xylanase (I) and (ii) the native *Thermomyces lanuginosus* xylanase (II) are shown. The results are based on two, similar, dosages of 0.65 and 2.58 FXU/g wheat. From the figure it appears that the effect on viscosity in wheat suspensions are quite similar.

In summary this example clearly demonstrates that when compared to a state of the art feed additive, the xylanases derived from *Thermomyces lanuginosus* are superior in reducing the viscosity of a wheat suspension, and therefore posses great potential for use as feed enhancing enzymes.

EXAMPLE 7

*Thermomyces lanuginosus* Xylanase as Feed Enhancing Enzyme

In this example, a *Thermomyces lanuginosus* monocomponent xylanase preparation is added to animal feed and compared to a conventional digestibility increasing enzyme preparation.

The monocomponent xylanase preparation was obtained according to examples 1–3. The reference preparation is a state of the art feed additive, a multicomponent enzyme preparation obtained by cultivation of *Humicola insolens* (Bio-Feed Plus CT, a product of Novo Nordisk A/S, Denmark).

Broiler chickens were fed on an experimental diet with and without enzymes for three weeks. The composition of the diet is shown in Table 1, below.

Animals were divided into five main groups and subjected to five different treatments. Each main group was divided into eight subgroups (cages) consisting of 30 broilers (15 of each sex). Each subgroup (cage) was weighed separately.

The five different treatments included a control treatment without enzymes and the following enzyme additive treatments: 400 and 800 FXU/kg feed of reference preparation (Ref.), and 200 and 400 FXU/kg feed of the monocomponent xylanase preparation of the invention (Inv.).

TABLE 1

Feed Composition.

| Ingredients | % |
|---|---|
| Wheat, dehulled, toasted | 73.10 |
| Fish meal, low in ash | 12.50 |
| Meat-and-bone meal, low in ash | 4.00 |
| Animal fat | 4.00 |
| Methionine (40%) | 4.00 |
| Limestone | 0.45 |
| Dicalciumphosphate | 0.60 |
| Vitamins/micromineral premix | 0.75 |
| Choline chloride | 0.26 |
|  | 0.04 |
| Total | 100 |
| ME per kg feed, MJ | 12.85 |
| Protein, % | 19.77 |
| Per 10 MJME, g |  |
| Protein | 154 |
| Lysine | 7.26 |
| Threonine | 5.17 |
| Methionine + cystine | 6.31 |
| Arginine | 8.77 |
| Calcium | 7.27 |
| Phosphorus, available | 3.48 |
| Sodium | 1.53 |
| Chloride | 2.21 |

The treatment was initiated on day-old chicks. After three weeks of treatment, weight gain and feed consumption was measured, and a Feed Conversion Ratio (FCR) was calculated, cf. Table 2, below (in which the chick weight and the feed intake at three weeks age are presented).

It appears from Table 2 that FCR is lower in the groups receiving 200 FXU/kg feed of the enzyme preparation of the invention (nv.) when compared to the control group and the group receiving 400 FXU of reference preparation (Ref.). However, the FCR calculated after use of 200 FXU of the enzyme preparation of the invention is at the same level as after use of 800 FXU of the reference preparation, which indicates that when compared to the reference preparation, the enzyme preparation of the invention has the same effect at a ¼ FXU dose level.

Thus the enzyme of the invention is considered better at improving the digestibility of feedstuffs than the reference preparation. Although being a monocomponent preparation, the preparation of the invention is superior in increasing the digestibility when compared to a state of the art feed additive, which offers the action of multiple enzyme components.

TABLE 2

Production Parameters of from 0 to 3 Weeks.

|  |  | Weight/ Chick (g) | Feed Intake/ Chick (g) | Feed Conversion Ratio (g/g) |  |
|---|---|---|---|---|---|
| Control |  | 612 | 870 | 1.42 | 100 |
| Ref. | 400 | 587 | 839 | 1.42 | 100 |
|  | 800 | 634 | 878 | 1.38 | 97 |
| Inv. | 200 | 623 | 861 | 1.38 | 97 |
|  | 400 | 597 | 820 | 1.37 | 96 |

EXAMPLE 8

Improvement of the Metabolizable Energy of Wheat in Broiler Diets

This example demonstrates a comparison of two animal feed additives of the invention with a state of the art feed additive on the impact on the Apparent Metabolizable Energy (AME) value of wheat.

The two animal feed additives of the invention are (A) a *Thermomyces lanuginosus* monocomponent xylanase preparation obtained by recombinant DNA techniques according to examples 1–3, and (B) a native *Thermomyces lanuginosus* xylanase preparation obtained by the method described in Example 5. The state of the art feed additive is a multicomponent enzyme preparation (C) obtained by cultivation of Humicola insolens (Bio-Feed Plus CT, a product of Novo Nordisk A/S, Denmark).

Day-old male Ross broiler chicks, delivered from a commercial hatchery, were used. From days 1 to 16 they were fed a commercial starter diet. On day 16 they were weighed individually. Birds with too high or too low body weight were discarded and the rest were assigned to battery cages. From day 16 to day 23 they were adapted to the cages.

A balance trial was carried out from day 24 to 28 according to the European Reference Method for in vivo determination of metabolizable energy AME [Bourdillon et al.; *Br. Pouly. Sci.* 1990 31 557–565]. The trial included 9 treatments with 5 replicates of 4 broiler chicks per replicate.

The basal diet contained 56% sorghum, 32.5% soybean meal, 6% animal fat, 1% soybean oil and 5% minerals, vitamins, trace elements and amino acids. In the experimental diet, half of the basal diet was replaced by wheat. Chicks were fed with diets as mash at a level of 90% of ad libitum intake.

Excreta was collected quantitatively daily. Samples of feed and freezedried excreta were analyzed for fat, gross energy (GE) and nitrogen. The AME content of the diets were calculated from their respective excreta/feed ratio as well as their corresponding GE content. Correction for N-retention to zero (AMEn) was carried out using an energy equivalent of 34.36 kJ/g N retained. Fat digestibility was determined by fat extraction of diets and freezedried excreta, taking into account the excreta/feed ratio.

The results were analyzed by a one-factorial analysis of variance with significant differences identified by a LSD-multiple range test, using Statgraphics version 5. The results are shown in Table 3, below, and FIGS. 6–7.

FIG. 6 shows the AMEn value of wheat (MJ/kg) as a function of xylanase addition (FXU/kg feed); (A) *Thermomyces lanuginosus* monocomponent xylanase preparation; (B) native *Thermomyces lanuginosus* xylanase preparation; (C) reference (Bio-Feed Plus CT, a product of Novo Nordisk A/S, Denmark; a multicomponent enzyme preparation obtained by cultivation of *Humicola insolens*).

FIG. 7 shows the fat digestion (%) in the experimental diet, as a function of xylanase addition (FXU/kg feed); (A) *Thermomyces lanuginosus* monocomponent xylanase preparation; (B) native *Thermomyces lanuginosus* xylanase preparation; (C) reference (Bio-Feed Plus CT, a product of Novo Nordisk A/S, Denmark; a multicomponent enzyme preparation obtained by cultivation of *Humicola insolens*).

The supplementation of the basal diet with 200 FXU/kg feed of either of (A) or (B) resulted in a relatively small and non-significant increase of the AMEn average value as well as of the fat digestion (cf. Table 3). In consequence, no corrections are made for the activity of the xylanases on the basal components when calculating the AMEn values of wheat.

In the experimental diet both (A) and (B) were dosed as 100 and 200 FXU/kg feed, whereas (C) was dosed as 400 FXU/kg feed.

As can be seen from Table 3, both doses of the animal feed additives of the invention resulted in a significant better AMEn than the experimental diet alone. The AMEn of wheat shows improvements of from 4.9–8.6% after addition of the enzymes. The reference additive (C) shows an improvement on AMEn of wheat of 4.9%.

Comparing the animal feed additives of the invention with a state of the art additive, it is clear that the animal feed additives of the invention perform much better than the reference additive when dosed on an FXU basis. 200 FXU/kg of (B) are significantly better than 400 FXU/kg of (C).

The fat digestion of the experimental diet follows the same pattern as the AMEn values.

TABLE 3

| Treatment | Diet | | | | Wheat | |
|---|---|---|---|---|---|---|
| | Fat dig. (%) | AME (MJ/kg) | N-retention (kJ/kg) | AMEn (MJ/kg) | AMEn (MJ/kg) | Diff. (%) |
| Basal diet (D) | 73.6 ab | 13.14 ± 0.47 a | 607 ± 6 a | 12.53 ± 0.05 ab | — | — |
| D + (A) 200 FXU/kg | 73.1 ab | 13.19 ± 0.13 a | 604 ± 7 a | 12.59 ± 0.12 a | — | +0.66 |
| D + (B) 200 FXU/kg | 72.7 abc | 13.15 ± 0.13 a | 620 ± 20 a | 12.53 ± 0.12 ab | — | +0.03 |
| 50% D + 50% wheat (DW) | 69.1 ef | 12.32 ± 0.15 d | 427 ± 9 ef | 11.89 ± 0.15 e | 11.25 | — |
| DW + (C) 400 FXU/kg | 72.4 bcd | 12.62 ± 0.25 c | 455 ± 20 bcd | 12.16 ± 0.24 d | 11.80 | +4.85 |
| DW + (A) 100 FXU/kg | 72.1 bcd | 12.60 ± 0.07 c | 441 ± 18 cde | 12.16 ± 0.06 d | 11.80 | +4.89 |
| DW + (A) 200 FXU/kg | 73.5 ab | 12.75 ± 0.17 bc | 463 ± 12 b | 12.29 ± 0.17 cd | 12.05 | +7.11 |
| DW + (B) 100 FXU/kg | 72.6 abc | 12.64 ± 0.10 bc | 437 ± 14 de | 12.21 ± 0.09 cd | 11.89 | +5.65 |
| DW + (B) 200 FXU/kg | 74.3 a | 12.84 ± 0.12 b | 460 ± 14 bc | 12.38 ± 0.11 bc | 12.22 | +8.64 |

We claim:

1. A DNA construct comprising a DNA sequence encoding a xylanase comprising:

a) the xylanase encoding part of either the DNA sequence presented as SEQ ID NO: 1, or the DNA sequence obtainable from the plasmid in the strain *Saccharomyces cerevisiae* DSM 10133; or b) a DNA sequence analogue to the xylanase encoding part of either the DNA sequence presented as SEQ ID NO: 1, or to the DNA sequence obtainable from the plasmid in the strain *Saccharomyces cerevisiae* DSM 10133, which analogue DNA sequence either i) is 95% identical to the xylanase encoding part of either the DNA sequence presented as SEQ ID NO: 1, or to the DNA sequence obtainable from the plasmid in the strain *Saccharomyces cerevisiae* DSM 10133; or ii) hybridizes with a wash of 2x SSC and 0.2% SDS at 65° C. for 30 min with the xylanase encoding part of either the DNA sequence presented as SEQ ID NO: 1, or with the DNA sequence obtainable from the plasmid in the strain *Saccharomyces cerevisiae* DSM 10133; or iii) encodes a polypeptide which is at least 95% identical to the polypeptide encoded by the DNA sequence presented as SEQ ID NO: 1, or to the DNA sequence obtainable from the plasmid in the strain *Saccharomyces cerevisiae* DSM 10133.

2. The DNA construct of claim 1, in which the DNA sequence encoding the xylanase is derived from a strain of *Byssochlamus, Chaetomium, Humicola, Malbranchea, Mucor, Myceliophthora, Paecilomyces, Talaromyces, Thermoascus,* or *Thielavia.*

3. A recombinant expression vector comprising a DNA construct of claim 1.

4. A host cell comprising a DNA construct of claim 1.

5. The host cell according to claim 4, which is a eukaryotic cell.

6. The host cell according to claim 5, which cell belongs to a strain of *Aspergillus.*

7. A method of producing a xylanase, comprising (a) culturing the host cell of claim 4 under conditions permitting the production of the xylanase component, and (b) recoverying the xylanase from the culture.

* * * * *